(12) United States Patent
Amin et al.

(10) Patent No.: US 9,138,213 B2
(45) Date of Patent: Sep. 22, 2015

(54) HEART OCCLUSION DEVICES

(75) Inventors: Zahid Amin, Omaha, NE (US); Edward Cully, Flagstaff, AZ (US); Warren Cutwright, Flagstaff, AZ (US); Coby Larsen, Flagstaff, AZ (US); Steven Masters, Flagstaff, AZ (US); Edward Emil Shaw, Flagstaff, AZ (US)

(73) Assignee: W.L. Gore & Associates, Inc., Newark, DE (US)

( * ) Notice: Subject to any disclaimer, the term of this patent is extended or adjusted under 35 U.S.C. 154(b) by 877 days.

(21) Appl. No.: 13/210,198

(22) Filed: Aug. 15, 2011

(65) Prior Publication Data

US 2012/0071918 A1     Mar. 22, 2012

Related U.S. Application Data

(63) Continuation-in-part of application No. 12/400,445, filed on Mar. 9, 2009.

(60) Provisional application No. 61/034,772, filed on Mar. 7, 2008.

(51) Int. Cl.
*A61B 17/08* (2006.01)
*A61B 17/00* (2006.01)
*A61B 17/12* (2006.01)

(52) U.S. Cl.
CPC ....... *A61B 17/0057* (2013.01); *A61B 17/12022* (2013.01); *A61B 17/12122* (2013.01);
(Continued)

(58) Field of Classification Search
CPC ................ A61B 17/0057; A61B 17/12122; A61B 17/12145; A61B 17/12172; A61B 17/12022; A61B 2017/12095; A61B 2017/00557; A61B 2017/00592; A61B 2017/00606; A61B 2017/00632; A61B 2017/00615; A61B 2017/12054; A61B 2017/00243; A61B 2017/00575; A61B 2017/00597; A61B 2017/00623; A61B 2017/00867; A61B 2017/00853
See application file for complete search history.

(56) References Cited

U.S. PATENT DOCUMENTS 5,976,174 A * 11/1999 Ruiz .............................. 606/213
6,024,756 A *  2/2000 Huebsch et al. .............. 606/213
(Continued)

FOREIGN PATENT DOCUMENTS

DE    102006036649    10/2007
EP         2340770     7/2011
(Continued)

OTHER PUBLICATIONS

International Search Report and Written Opinion for PCT/US2014/017129 mailed May 14, 2014, 9 pages.
(Continued)

*Primary Examiner* — Gregory Anderson
*Assistant Examiner* — Son Dang
(74) *Attorney, Agent, or Firm* — Fish & Richardson P.C.

(57) ABSTRACT

The disclosure is directed to a heart occlusion device and a method for occluding an aperture defect in a heart. The heart occlusion device includes two separate wires 12, 14. Each wire forms geometric shapes that together form a distal plate and a proximal plate. The first plate is disposed in a first plane. The second plate is disposed in a second plane that is parallel to and remote from the first plane. The distal plate and the proximal plate are separated by a self-centering waist. The proximal plate is attached to a hub. A similar hub is optional on the distal plate. The plates further include coverings which form a sealant to occlude an aperture in a tissue. The wires forming the plates have a shape-memory capability such that they can be collapsed and distorted in a catheter during delivery but resume and maintain their intended shape after delivery.

43 Claims, 21 Drawing Sheets

(52) U.S. Cl.
CPC ..... *A61B17/12145* (2013.01); *A61B 17/12172* (2013.01); *A61B 2017/00243* (2013.01); *A61B 2017/00557* (2013.01); *A61B 2017/00575* (2013.01); *A61B 2017/00592* (2013.01); *A61B 2017/00597* (2013.01); *A61B 2017/00606* (2013.01); *A61B 2017/00623* (2013.01); *A61B 2017/00632* (2013.01); *A61B 2017/00867* (2013.01); *A61B 2017/1205* (2013.01)

(56) References Cited

U.S. PATENT DOCUMENTS

| | | | |
|---|---|---|---|
| 6,214,029 B1* | 4/2001 | Thill et al. | 606/213 |
| 6,270,515 B1* | 8/2001 | Linden et al. | 606/213 |
| 6,355,052 B1* | 3/2002 | Neuss et al. | 606/213 |
| 6,375,671 B1* | 4/2002 | Kobayashi et al. | 606/213 |
| 6,554,849 B1 | 4/2003 | Jones et al. | |
| 7,207,402 B2 | 4/2007 | Bjoerk | |
| 7,335,426 B2 | 2/2008 | Marton et al. | |
| 7,658,748 B2* | 2/2010 | Marino et al. | 606/213 |
| 7,842,053 B2* | 11/2010 | Chanduszko et al. | 606/157 |
| 7,871,419 B2 | 1/2011 | Devellian | |
| 7,887,562 B2* | 2/2011 | Young et al. | 606/213 |
| 8,308,760 B2* | 11/2012 | Chanduszko | 606/215 |
| 8,753,362 B2* | 6/2014 | Widomski et al. | 606/151 |
| 8,821,528 B2* | 9/2014 | McGuckin et al. | 606/200 |
| 8,858,576 B2 | 10/2014 | Takahashi et al. | |
| 2002/0111647 A1 | 8/2002 | Khairkhahan et al. | |
| 2003/0130683 A1 | 7/2003 | Andreas et al. | |
| 2003/0171774 A1* | 9/2003 | Freudenthal et al. | 606/213 |
| 2003/0191495 A1* | 10/2003 | Ryan et al. | 606/213 |
| 2003/0225421 A1* | 12/2003 | Peavey et al. | 606/151 |
| 2003/0225439 A1 | 12/2003 | Cook et al. | |
| 2004/0073242 A1* | 4/2004 | Chanduszko | 606/157 |
| 2004/0133230 A1 | 7/2004 | Carpenter et al. | |
| 2004/0176799 A1* | 9/2004 | Chanduszko et al. | 606/213 |
| 2004/0254594 A1 | 12/2004 | Alfaro | |
| 2005/0043759 A1* | 2/2005 | Chanduszko | 606/213 |
| 2005/0187564 A1 | 8/2005 | Jayaraman | |
| 2005/0187568 A1 | 8/2005 | Klenk et al. | |
| 2005/0192626 A1 | 9/2005 | Widomski et al. | |
| 2005/0267523 A1* | 12/2005 | Devellian et al. | 606/213 |
| 2005/0267525 A1* | 12/2005 | Chanduszko | 606/213 |
| 2005/0288706 A1 | 12/2005 | Widomski et al. | |
| 2005/0288786 A1* | 12/2005 | Chanduszko | 623/11.11 |
| 2006/0025790 A1 | 2/2006 | de Winter et al. | |
| 2006/0116710 A1* | 6/2006 | Corcoran et al. | 606/200 |
| 2006/0122647 A1* | 6/2006 | Callaghan et al. | 606/213 |
| 2006/0167494 A1 | 7/2006 | Suddaby | |
| 2007/0265656 A1 | 11/2007 | Amplatz et al. | |
| 2008/0065149 A1 | 3/2008 | Thielen et al. | |
| 2008/0208214 A1 | 8/2008 | Sato et al. | |
| 2008/0228218 A1* | 9/2008 | Chanduszko | 606/215 |
| 2009/0062844 A1* | 3/2009 | Tekulve et al. | 606/213 |
| 2009/0204133 A1* | 8/2009 | Melzer et al. | 606/158 |
| 2009/0228038 A1 | 9/2009 | Amin et al. | |
| 2009/0292310 A1* | 11/2009 | Chin et al. | 606/215 |
| 2010/0234885 A1* | 9/2010 | Frazier et al. | 606/213 |
| 2011/0054519 A1 | 3/2011 | Neuss | |
| 2012/0245623 A1* | 9/2012 | Kariniemi et al. | 606/213 |
| 2012/0316597 A1* | 12/2012 | Fitz et al. | 606/194 |
| 2013/0165967 A1 | 6/2013 | Amin et al. | |

FOREIGN PATENT DOCUMENTS

| | | |
|---|---|---|
| JP | 2000505668 T | 5/2000 |
| JP | 2000300571 A5 | 8/2004 |
| JP | 2005521818 T | 7/2005 |
| JP | 2004534390 A5 | 12/2005 |
| JP | 2005521447 A5 | 5/2006 |
| JP | 2006230800 A | 9/2006 |
| SU | 1377052 | 2/1988 |
| WO | WO03/103476 | 12/2003 |
| WO | WO2004012603 A3 | 5/2004 |
| WO | WO 2008153872 | 12/2008 |
| WO | WO2007124862 A8 | 1/2009 |

OTHER PUBLICATIONS

Chinese Search Report in Application No. 200980158768.9, dated Jun. 16, 2013, 4 pages.
International Preliminary Report on Patentability and Written Opinion for PCT/US2009/004307, mailed Sep. 13, 2011, 8 pages.
International Search Report for PCT/US2009/004307, mailed Nov. 27, 2009, 6 pages.
International Search Report for PCT/US2012/050785, mailed Nov. 23, 2012, 6 pages.

* cited by examiner

HEART OCCLUSION DEVICES

CROSS-REFERENCES TO RELATED APPLICATIONS

This is a continuation-in-part of application Ser. No. 12/400,445, filed Mar. 9, 2009, which claims priority to U.S. Provisional Application Ser. No. 61/034,772, filed Mar. 7, 2008, both of which are incorporated herein by reference in their entireties.

FIELD OF THE INVENTION

The present invention is directed to a medical device and particularly to a device for closing congenital cardiac defects. The present invention is specifically directed to a heart occlusion device with a self-centering mechanism.

DESCRIPTION OF THE PRIOR ART

Heart occlusion devices for correcting congenital heart defects, such as atrial septal defects ("ASD"), patent foramen ovale ("PFO") defects, ventricular septal defects ("VSD"), and patent ductus arteriosus ("PDA") defects, are known to the medical field. The following companies manufacture different types of devices: AGA Medical, Microvena Corp./EV3 Medical, Velocimed/St. Jude Medical, Occlutech International, NMT Medical, Cardia, Inc., Solysafe S A, Sideris (Custom Medical, Inc.), W L Gore, and Cook, Inc.

A specific example of one such heart defect is a PFO. A PFO, illustrated in FIG. 1 at 6A, is a persistent, one-way, usually flap-like opening in the wall between the right atrium 2 and left atrium 3 of the heart 1. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 2 to the left atrium 3, and blood clots could enter the systemic circulation. It is desirable that this circumstance be eliminated.

The foramen ovale 6A serves a desired purpose when a fetus is gestating in utero. Because blood is oxygenated through the umbilical chord and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 8 and septum secundum 9. However, a PFO has been shown to persist in a number of adults.

The presence of a PFO defect is generally considered to have no therapeutic consequence in otherwise healthy adults. Paradoxical embolism via a PFO defect is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO defect and the risk for paradoxical embolism or stroke. In addition, there is significant evidence that patients with a PFO defect who have had a cerebral vascular event are at increased risk for future, recurrent cerebrovascular events.

Accordingly, patients at such an increased risk are considered for prophylactic medical therapy to reduce the risk of a recurrent embolic event. These patients are commonly treated with oral anticoagulants, which potentially have adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close a PFO defect. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOB. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are not insignificant complications due to thrombus, fractures of the components, conduction system disturbances, perforations of heart tissue, and residual leaks. Many devices have high septal profile and include large masses of foreign material, which may lead to unfavorable body adaptation of a device. Given that ASD devices are designed to occlude holes, many lack anatomic conformability to the flap-like anatomy of PFOB. The flap-like opening of the PFO is complex, and devices with a central post or devices that are self-centering may not close the defect completely, an outcome that is highly desired when closing a PFO defect. Hence, a device with a waist which can conform to the defect will have much higher chance of completely closing the defect. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

Devices for occluding other heart defects, e.g., ASD, VSD, PDA, also have drawbacks. For example, currently available devices tend to be either self-centering or non-self-centering and may not properly conform to the intra-cardiac anatomy. Both of these characteristics have distinct advantages and disadvantages. The non-self centering device may not close the defect completely and may need to be over-sized significantly. This type of device is usually not available for larger defects. Further, the self-centering device, if not sized properly, may cause injury to the heart.

Some have sharp edges, which may damage the heart causing potentially clinical problems.

Some devices contain too much nitinol/metal, which may cause untoward reaction in the patient and hence can be of concern for implanting physicians and patients.

Some currently marketed devices have numerous model numbers (several available sizes), making it difficult and uneconomical for hospitals and markets to invest in starting a congenital and structural heart interventional program.

The present invention is designed to address these and other deficiencies of prior art aperture closure devices. Furthermore, other desirable features and characteristics of the present invention will become apparent from the subsequent detailed description and the appended claims, taken in conjunction with the accompanying drawings and this section.

SUMMARY OF THE INVENTION

The present invention is directed to a heart occlusion device with a self-centering mechanism comprising two separate, uniquely-shaped wires wherein each wire is shaped into two semi-circular designs to form two half-discs by the memory-shaping capability of the wires, a self-centering waist area formed between the two semi-circular designs, and a covering over the each of the two semi-circular designs, wherein the covering is a sealant from the heart occlusion.

More specifically, the present invention is directed to a device for occluding an aperture in tissue comprising a first flexible wire and a second flexible wire, wherein each of the first and second wires is comprised of a shape memory properties, and wherein each of the first and second wires is shaped into first and second generally semi-circular forms such that the first semicircular form of the first wire opposes the first semicircular form of the second wire to form a first disc and the second semicircular form of the first wire opposes the second semicircular form of the second wire to form a second disc wherein further each of the first and second discs is separated by a self-centering waist formed from two sections of the first wire and two sections of the second wire; and a sealed covering over each of the first and second discs, wherein the covering provides a seal to occlude the aperture.

The present invention is also directed to a device for occluding an aperture in a heart tissue comprising a first flexible wire and a second flexible wire. Each of the first and second wires is comprised of a shape memory property. Further, each of the first and second wires is shaped into first and second generally semi-circular forms such that the first semicircular form of the first wire opposes the first semicircular form of the second wire to form a first disc and the second semicircular form of the first wire opposes the second semicircular form of the second wire to form a second disc. Each of the first and second discs is separated by a self-centering waist formed from two sections of the first wire and two sections of the second wire, and wherein the two sections of the first wire and two sections of the second wire create an outward radial force to maintain the self-centering configuration of the device. Each of the first and second wires has a first and second end and wherein each of the first and second ends of the first and second wires is connected to a hub, wherein the hub further comprises a delivery attachment mechanism for attachment to a deployment cable. The device also includes a sealed covering over each of the first and second discs, wherein the covering provides a seal to occlude the aperture wherein the coverings comprise a flexible, biocompatible material capable of promoting tissue growth and/or act as a sealant.

The present invention is also directed to a method for inserting the occluder device described above into an aperture defect in a heart to prevent the flow of blood therethrough. The method comprises:

a. attaching the occluder device to a removable deployment cable,
b. placing the occluding device within a flexible delivery catheter having an open channel,
c. feeding the catheter into a blood vessel and advancing the catheter via the blood vessel system to the aperture defect in the heart,
d. advancing the catheter through the aperture defect,
e. withdrawing the catheter from the occluder device such that the first disc of the occluder device expands on one side of the aperture defect,
f. further withdrawing the catheter from the occluder device such that the second disc of the occluder device expands of the other side of the aperture defect, such that the waist of the occluder device expands by memory retention within the aperture defect to self-center the occluder device,
g. further withdrawing the catheter from the blood vessel; and
h. removing the deployment cable from the hub.

Advantages

The device of the present invention has many advantages:

Lower Profile: The occluder device of the present invention has a lower profile than available devices.

Conformable: The device is flexible and conformable to the patient anatomy, specifically the hole that is being closed. There are no sharp edges. The device is soft and hence less traumatic to the atrial tissue.

Self-Centering on Demand: Because of the unique way the two discs are connected, the device has self-centering characteristics. The uniqueness of this device is in the self-centering mechanism. The waist of the device is made of four wires. The wires will have the capability to conform to the shape and size of the defect in the organ—a characteristic not seen in prior art devices. Therefore, the self-centering of the device is dependent upon the size and the shape of the defect. The wires will have enough radial force to maintain the self-centering configuration but will not be strong enough to press against the defect edges in a manner that exacerbates the defect. The device is fully repositionable and retrievable after deployment.

Custom Fit: The device has the further ability to be custom-fit within the defect with balloon-expansion of the waist. Because of the self-expanding nature of the waist, this will not be needed in most cases. However, in cases in which custom expansion is needed (oval defects, tunnel defects), the waist size can be increased to conform to the defect by the balloon catheter expansion. A balloon may be inserted through a hollow screw attachment on the device's delivery hub and delivery cable. The expansion will be possible before the release of the device, which will increase the margin of safety.

Fewer Sizes: The expandable waist requires fewer sizes to close a wider variety of differently-sized defects. Thus, a single device may offer physicians the ability to implant devices in several different sizes.

The device will be less thrombogenic as the discs will be covered with ePTFE. The ePTFE has been time-tested and found to be least thrombogenic. There is the ability to close defects up to 42 mm with very mild modifications.

Security: There will be the opportunity to remain tethered to the implanted device before releasing it, which is an extra security feature.

Uses:

The device of the present invention should be appropriate for an ASD (atrial septal defect), PFO (patent foramen ovale), VSD (ventricular septal defect), and PDA (patent ductus arteriosus) with minor modifications. One skilled in the art would also recognize the device's application for use as a vascular occluder or plug as well as an atrial appendage occluder.

An important use of the device will also be in closure of an aperture in a left atrial appendage. The device can be modified to conform to the atrial appendage anatomy. The discs are modified so that the device is not extruded out with the heartbeats. Yet, the device is still soft enough to form adequate closure.

The discs can also be modified so that they become compatible for closure of veins and arteries. For this use, the connecting waist will become equivalent (or near equivalent) to the diameter of the discs. Other important uses will be in closure of coronary artery fistulas, arteriovenous fistulas, arteriovenous malformations, etc.

The objects and advantages of the invention will appear more fully from the following detailed description of the preferred embodiment of the invention made in conjunction with the accompanying drawings.

In accordance with an exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms such that the first geometric form of the first wire and the first geometric form of the second wire form a first plate in a first plane. The first plate has a center. The second geometric form of the first wire and the second geometric form of the second wire form a second plate in a second plane that is parallel to and remote from the first plane. The first and second plates are separated by a waist formed from two portions of the first wire and two portions of the second wire. The waist is offset from the center of the first plate.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms around an inner region such that the first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire. The waist comprises a first portion and a second portion. The first portion is connected to the inner region by a first segment. The second portion is connected to the inner region by a second segment. The first segment has a first length, and the second segment has a second length that is greater than the first length.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire. The first and second geometric forms comprise a first segment, a second segment, a third segment, and a fourth segment. The first segment is formed from a first of the two portions of the first wire. The first segment has a first length. The second segment is formed from a first of the two portions of the second wire. The second segment has a second length that is substantially equal to the first length. The third segment is formed from a second of the two portions of the first wire. The third segment generally opposes the first segment. The third segment has a third length that is greater than the first length. The fourth segment is formed from a second of the two portions of the second wire. The fourth segment generally opposes the first segment. The fourth segment has a fourth length that is substantially equal to the third length.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire. The first and second geometric forms comprise a first segment and a second segment. The first segment is formed from a first of the two portions of the first wire. The first segment has a first arm and a second arm. The first arm has a first length, and the second arm has a second length. The second length is greater than the first length. The second segment is formed from a first of the two portions of the second wire. The second segment has a third arm and a fourth arm. The third arm has the first length, and the fourth arm has the second length.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is parallel to and remote from the first plane. The first plate has a first surface area. The second plate has a second surface area that is greater than the first surface area. The first and second plates are separated by a waist formed from two portions of the first wire and two portions of the second wire.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is parallel to and remote from the first plane.

The first and second plates are separated by a waist formed from two portions of the first wire and two portions of the second wire. The waist has a length that is greater than eight millimeters.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is parallel to the first plane and greater than eight millimeters from the first plane. The first and second plates are separated by a waist formed from two portions of the first wire and two portions of the second wire.

In accordance with another exemplary embodiment, a device for occluding an aperture in tissue is provided. The device comprises a first flexible wire, a second flexible wire, and a hook. Each of the first and second wires is comprised of a shape memory material. Each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is parallel to the first plane. The first and second plates are separated by a waist formed from two portions of the first wire and two portions of the second wire. The hook is coupled to the first plate, and is configured for engagement with a positioning system.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms. The first geometric form of the first wire overlaps with the first geometric form of the second wire to form a first plate in a first plane. The second geometric form of the first wire overlaps with the second geometric form of the second wire to form a second plate in a second plane that is parallel to and remote from the first plane. The first and second plates are separated by a waist formed from two portions of the first wire and two portions of the second wire.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms separated by a waist formed from two portions of the first wire and two portions of the second wire. The first geometric form of the first wire and the first geometric form of the second wire form a first plate in a first plane. The second geometric form of the first wire and the second geometric form of the second wire form a second plate in a second plane that is parallel to and remote from the first plane. The first plane has a first quadrant, a second quadrant that is adjacent to the first quadrant, a third quadrant that is below the first quadrant, and a fourth quadrant that is below the second quadrant and adjacent to the third quadrant. The first geometric form of the first wire extends through the first, second, and third quadrants of the first plane. The first geometric form of the second wire extends through the first, third, and fourth quadrants of the first plane.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire. The first plate and the second plate form a non-zero angle with respect to one another.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are not substantially parallel to one another and are separated by a waist formed from two portions of the first wire and two portions of the second wire.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from a first waist component of the first wire and a second waist component of the second wire, the first and second waist components being of unequal sizes.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from a first waist component of the first wire and a second waist component of the second wire. The first and second waist components are configured to generate a non-zero angle of curvature for the waist.

In accordance with another exemplary embodiment, a device for occluding an aperture in tissue is provided. The device comprises a first flexible wire and a second flexible wire. Each of the first and second wires is comprised of a shape memory material. Each of the first and second wires is shaped into first and second geometric forms between their respective first and second ends. The first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire. The first end of the first wire is disposed at a first hub. At least one of the second end of the first wire, the first end of the second wire, and the second end of the second wire is disposed at a second hub.

In accordance with another exemplary embodiment, a device for occluding an aperture in tissue is provided. The device comprises a first flexible wire, a second flexible wire, and a third flexible wire. Each of the first, second, and third wires is comprised of a shape memory material. Each of the first, second, and third wires is shaped into first and second geometric forms. The first geometric form of the first wire, the first geometric form of the second wire, and the first geometric form of the third wire form a first plate. The second geometric form of the first wire, the second geometric form of the second wire, and the second geometric form of the third wire form a second plate. The first and second plates are separated by a waist formed from two portions of the first wire, two portions of the second wire, and two portions of the third wire.

In accordance with another exemplary embodiment, a method for occluding an aperture defect in a heart to prevent the flow of blood therethrough is provided. The method comprises the steps of providing an occluder device comprising a first flexible wire and a second flexible wire. Each of the first and second wires is comprised of a shape memory material. Each of the first and second wires is shaped into first and second geometric forms around an inner region such that the first geometric form of the first wire and the first geometric form of the second wire form a first plate in a first plane, and the second geometric form of the first wire and the second geometric form of the second wire form a second plate in a second plane that is parallel to and remote from the first plane. The first and second plates are separated by a waist formed from two portions of the first wire and two portions of the second wire. The occluder device further comprises a sealed covering over at least one of the first and second plates, wherein the covering provides a seal for the aperture defect. Each of the first and second wires has a first and second end. Each of the first and second ends of the first and second wires is connected to a hub. The hub further comprises a delivery attachment mechanism for attachment to a removable deployment cable. The method further comprises attaching the occluder device to the removable deployment cable, placing the occluder device within a flexible delivery catheter having an open channel, feeding the catheter into a blood vessel system and advancing the catheter via the blood vessel system to the aperture defect in the heart. The catheter is advanced through the aperture defect, and is withdrawn from the occluder device such that the first plate of the occluder device expands on a first side of the aperture defect. The catheter is further withdrawn from the occluder device such that the second plate of the occluder device expands on a second side of the aperture defect, such that the waist of the occluder device expands by memory retention within the aperture defect to self-center the occluder device. The catheter is further withdrawn from the blood vessel system, and the deployment cable is removed from the hub.

DETAILED DESCRIPTION OF THE INVENTION

The following detailed description is merely exemplary in nature and is not intended to limit the disclosure or the application and uses of the disclosure. Furthermore, there is no intention to be bound by any theory presented in the preceding background information or the following detailed description.

The present invention provides a device for occluding an aperture within body tissue. One skilled in the art will recognize that the device and methods of the present invention may be used to treat other anatomical conditions in addition to those specifically discussed herein. As such, the invention should not be considered limited in applicability to any particular anatomical condition.

Figure 1:
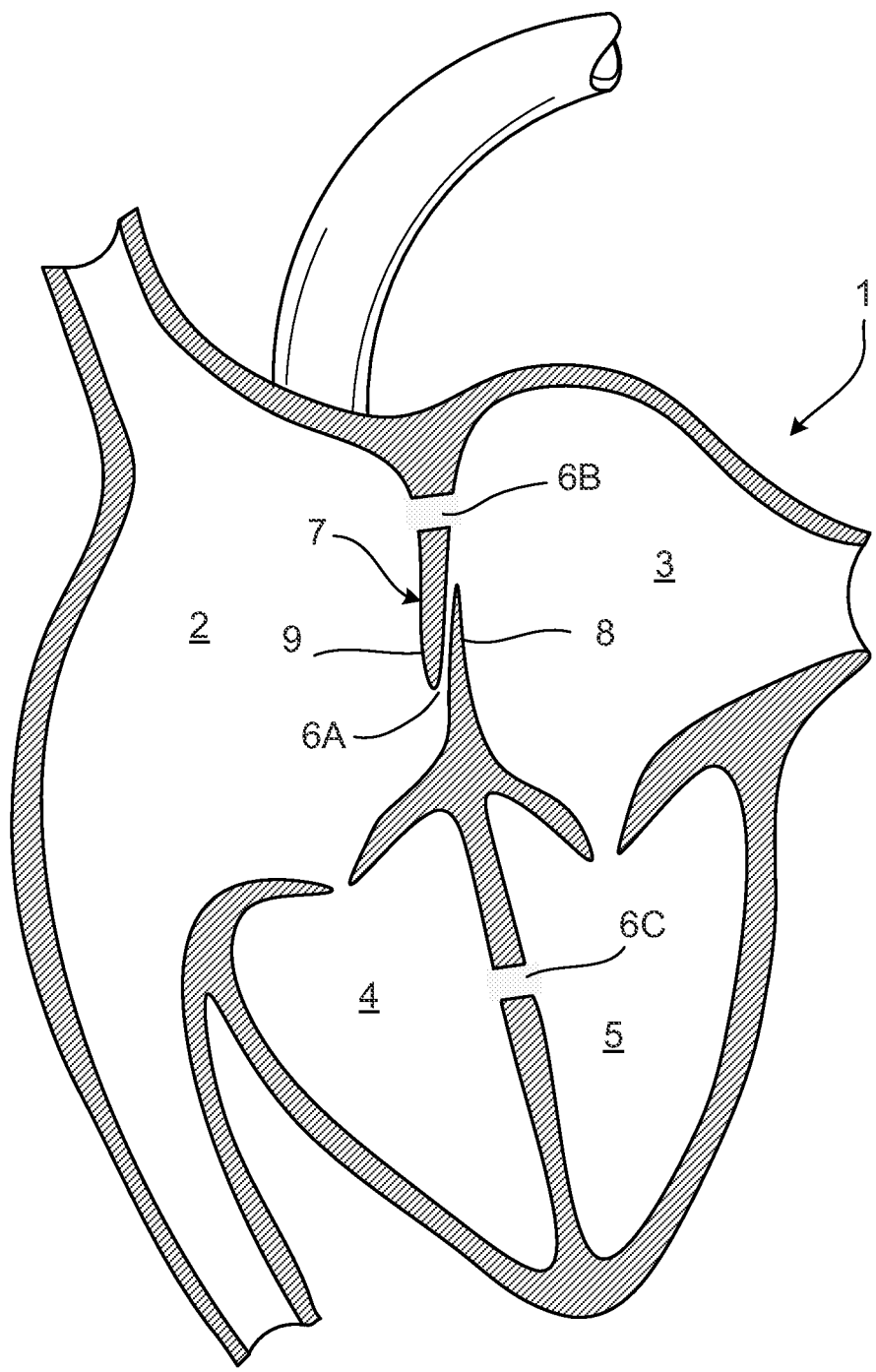
FIG. 1 is a schematic representation of a human heart including various septal defects.

FIG. 1 illustrates a human heart 1, having a right atrium 2, a left atrium 3, a right ventricle 4, and a left ventricle 5. Shown are various anatomical anomalies 6A, 6B, and 6C. The atrial septum 7 includes septum primum 8 and septum secundum 9. The anatomy of the septum 7 varies widely within the population. In some people, the septum primum 8 extends to and overlaps with the septum secundum 9. The septum primum 8 may be quite thin. When a PFO is present, blood could travel through the passage 6A between septum primum 8 and septum secundum 9 (referred to as "the PFO tunnel"). Additionally or alternatively, the presence of an ASD could permit blood to travel through an aperture in the septal tissue, such as that schematically illustrated by aperture 6B. A VSD is similar to an ASD, except that an aperture 6C exists in the septum between the left and right ventricle of the heart.

PDA results from defects in the ductus arteriosus. The human blood circulation comprises a systemic circuit and a pulmonary circuit. In the embryonic phase of human development, the two circuits are joined to one another by the ductus arteriosus. The ductus connects the aorta (circulation to the body) to the pulmonary artery (pulmonary circuit). In normal development of an infant, this ductus closes after birth. If development is defective, it can happen that the ductus does not close, and as a result the two blood circuits are still joined even after birth.

Unless specifically described otherwise, "aperture" 6 will refer to the specific heart defects described above, including PFO 6A, ASD 6B, VSD 6C, and PDA among others.

As used herein, "distal" refers to the direction away from a catheter insertion location and "proximal" refers to the direction nearer the insertion location.

As used herein, "memory" or "shape memory" refers to a property of materials to resume and maintain an intended shape despite being distorted for periods of time, such as during storage or during the process of delivery in vivo.

Referring now to FIGS. 2-5, the occluder device 10 of the present invention comprises two separate uniquely shaped memory wires 12, 14. The wire can be formed of biocompatible metals or polymers, such as bioresorbable polymers, shape memory polymers, shape memory metal alloys, biocompatible metals, bioresorbable metals, or combinations thereof. Specific examples include but are not limited to iron, magnesium, stainless steel, nitinol, or combinations of these and similar materials. A preferred metal for the present invention is a nitinol alloy. Nitinol (an acronym for Nickel Titanium Naval Ordnance Laboratory) is a family of intermetallic materials, which contain a nearly equal mixture of nickel (55 wt. %) and titanium. Other elements can be added to adjust or "tune" the material properties. Nitinol exhibits unique behavior, specifically, a well defined "shape memory" and super elasticity. In general, any biocompatible material with a memory capability can be used with the present invention. The thermal shape memory and/or superelastic properties of shape memory polymers and alloys permit the occluder 10 to resume and maintain its intended shape in vivo despite being distorted during the delivery process. In certain embodiments, the memory may also assist in pressing an aperture, such as a PFO tunnel, closed. The diameter or thickness of the wire depends on the size and type of the device, i.e., the larger the device, the larger the diameter of the wire. In general, wire having a diameter between about 0.2 mm and 0.8 mm can be used. As described further below in connection with FIGS. 12A, 12B, and 22, in certain embodiments more than two wires may be utilized.

The first wire 12 forms one or more first geometric forms 12A and one or more second geometric forms 12B. "Geometric forms" as used herein comprises symmetric as well as asymmetric forms. Relative to a delivery attachment mechanism or hub 30, discussed below in greater detail, the first geometric form 12A of the first wire 12 preferably comprises a distal geometric form, and the one or more second geometric forms 12B of the first wire preferably each comprise proximal geometric forms. In the embodiment of FIGS. 2-5, there is a single first, or distal, geometric form 12A of the first wire 12. Also in the embodiment of FIGS. 2-5, there are two second, or proximal, geometric forms 12B of the first wire 12 (namely, 12B(A) and 12B(B)). However, the number and configuration of the first and/or second geometric forms 12A, 12B of the first wire 12 may vary.

Similarly, the second wire 14 forms a first geometric form 14A and a second geometric form 14B. Relative to the hub 30, the first geometric form 14A of the second wire 14 preferably comprises a distal geometric form, and the second geometric form 14B of the second wire preferably comprises a proximal geometric form. In the embodiment of FIGS. 2-5, there is a single first, or distal, geometric form 14A of the second wire 14. Also in the embodiment of FIGS. 2-5, there are two second, or proximal, geometric forms 14B of the second wire 14 (namely, 14B(A) and 14B(B)). However, the number and configuration of the first and/or second geometric forms 14A, 14B of the second wire 14 may vary.

The first geometric forms 12A of the first wire 12 and the first geometric forms 14A of the second wire 14 form a first plate, such as a disc, or another otherwise relatively flat surface (hereinafter referred to as a "plate") 16 in a first plane 218. The second geometric forms 12B of the first wire 12 and the second geometric forms 14B of the second wire 14 form a second plate 18 (also referred to as a "disc" in certain embodiments) in a second plane 220 that is parallel to and remote from the first plane 218. In the embodiment of FIGS. 2-5, the first and second plates 16, 18 each comprise one or more semi-circular discs (as described directly below). However, this may vary in other embodiments, for example as described further below in connection with FIGS. 21A-21E.

As shown in FIGS. 2-5, in these embodiments, each wire 12 or 14 forms a shape which mirrors that of the respective wire 14 or 12. Specifically, each wire 12, 14 forms a distal semi-circle or half-disc 12A, 14A in addition to two proximal quarter-circles or quarter-discs 12B, 12B' or 14B, 14B'. The two proximal quarter-circles of each wire together form proximal semi-circles or half-discs 12B, 12B' or 14B, 14B'. The two distal semi-circles of each respective wire 12A, 14A together comprise a distal circle or distal disc 16 of the occluder 10. The four proximal quarter-circles 12B, 12W, 14B, 14W, which form a "four-leaf clover" configuration, comprise a proximal circle or proximal disc 18 of the occluder 10.

Figure 2:
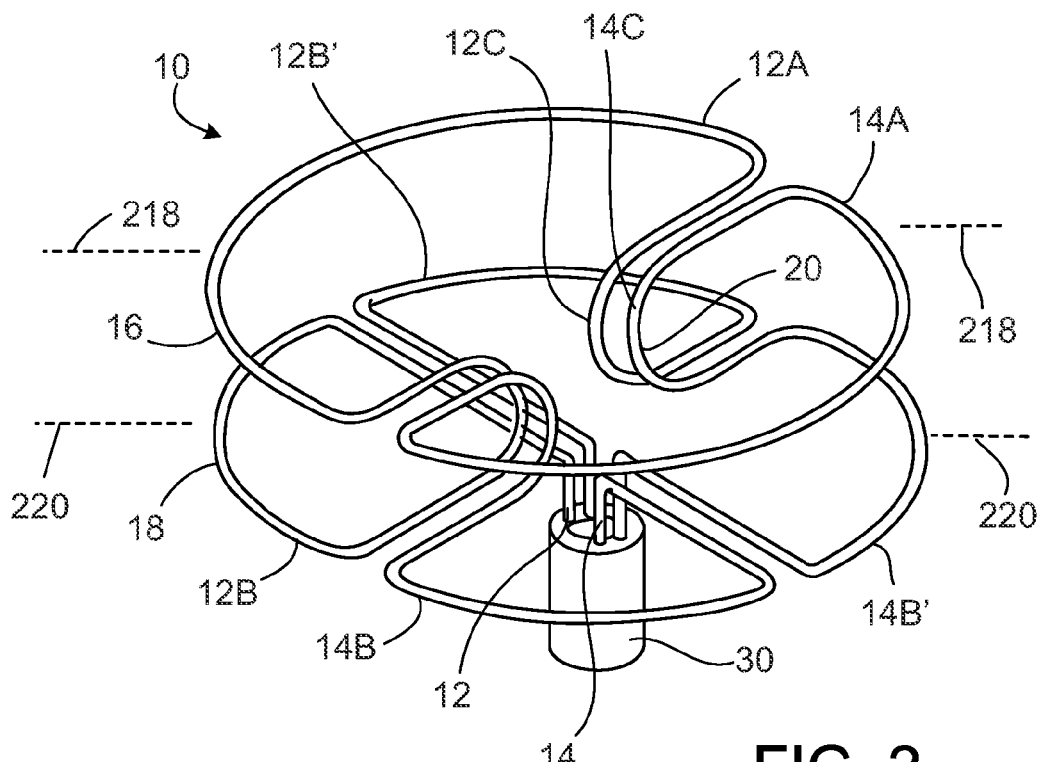
FIG. 2 is a perspective view of the occluder device of the present invention.
Figure 3:
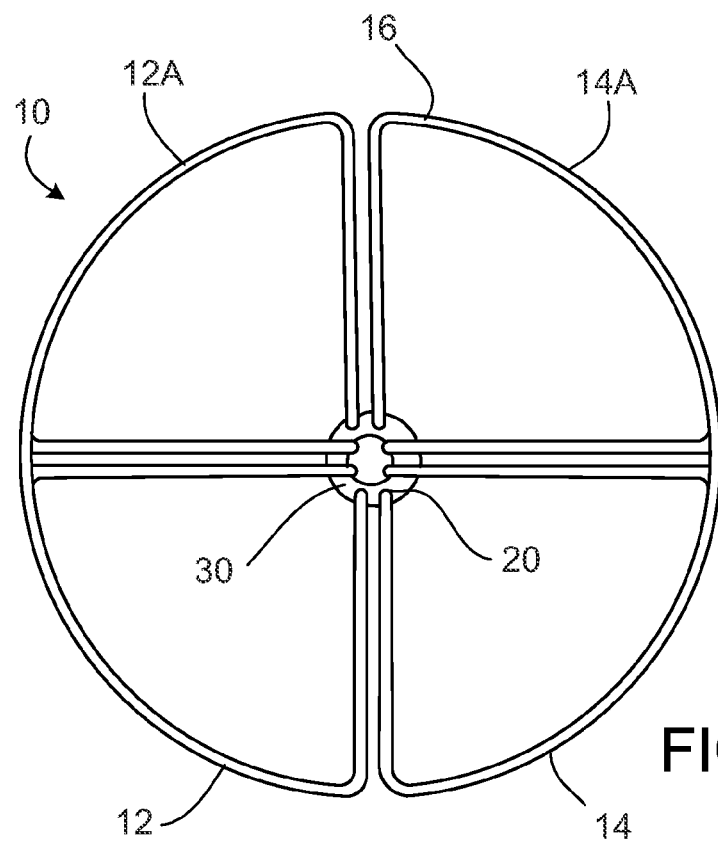
FIG. 3 is a top plan view of the occluder device of FIG. 2.
Figure 4:
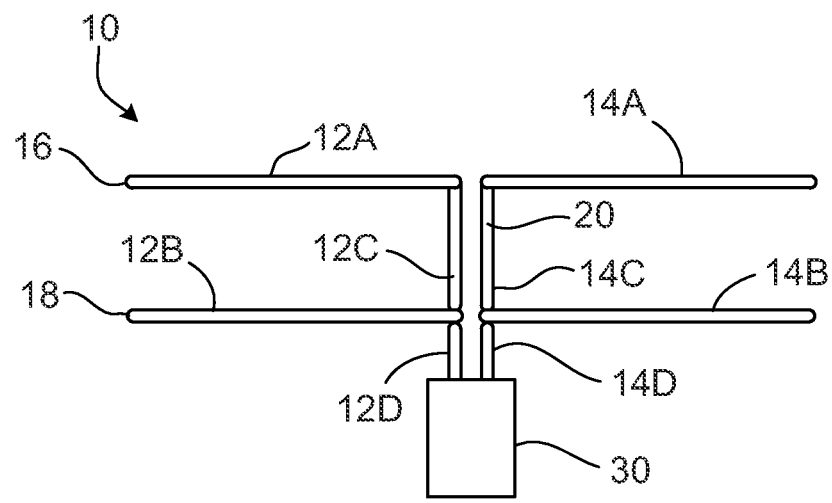
FIG. 4 is a side plan view of the occluder device taken along lines in FIG. 2.
Figure 5:
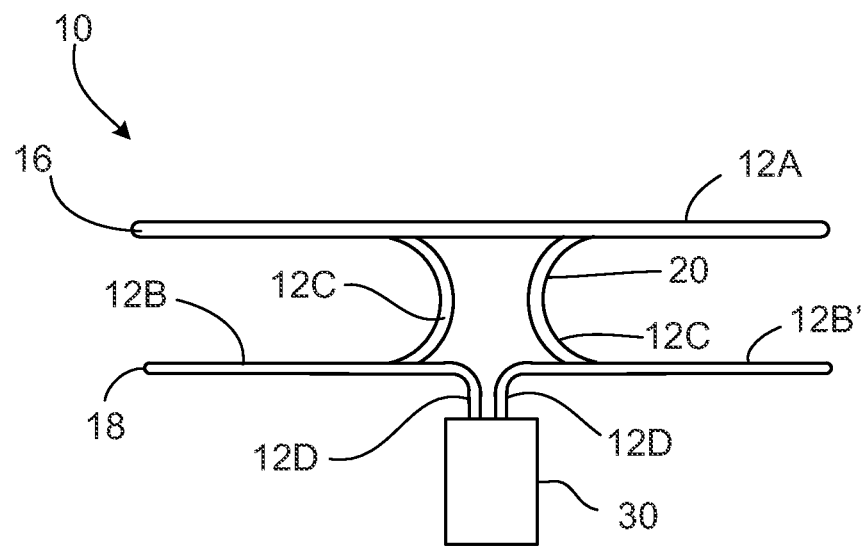
FIG. 5 is a side plan view of the occluder device taken along in FIG. 2.

The proximal semi-circle 12B, 12B' or 14B, 14B' of each wire is connected to the distal semi-circle 12A or 14A by waist portions (also referred to herein as waist components) 12C, 14C. As shown in FIG. 2, there are two waist portions 12C, 14C per wire. The four waist portions (two from each wire) 12C, 14C together comprise a restricted area or waist 20 of the occluder device 10. The distance between the waist portions, both within the same wire and from wire to wire, determines the size of the waist 20. The size of the waist 20 is dependent on the particular application and the size of the occluder device 10. The resiliency and memory of the waist portions 12C, 14C and capacity to expand radially serves as a self-centering mechanism of the occluder device 10 in apertures 6.

The Hub 30:

The two half-discs are not attached or joined to each other except at the junction of the delivery attachment mechanism or hub 30. The ends 12D, 14D of wires 12, 14 will be welded or otherwise connected to the hub 30.

Figure 6:
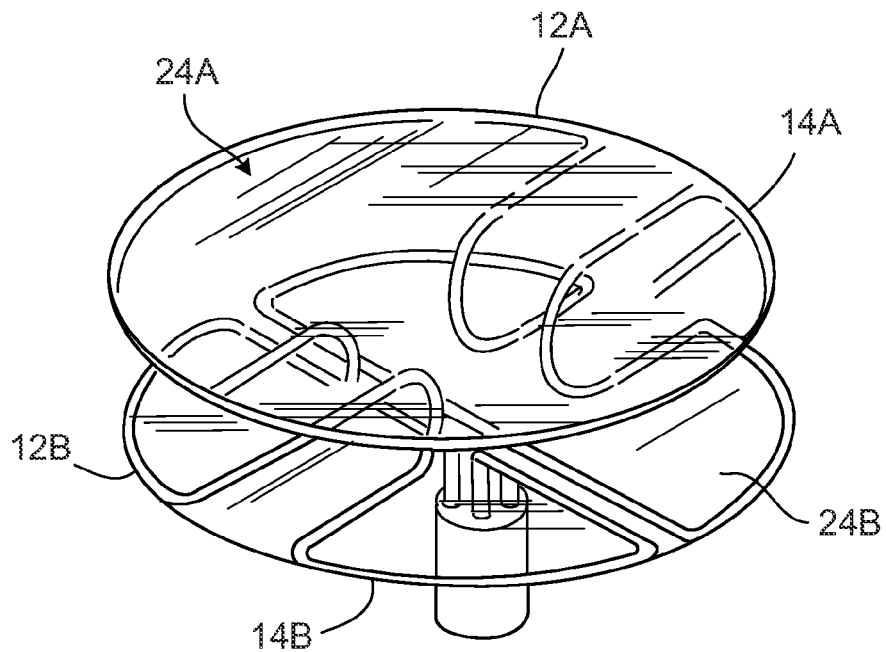
FIG. 6 is a perspective view of the occluder device of FIG. 2, illustrating the covering 42.
Figure 7:
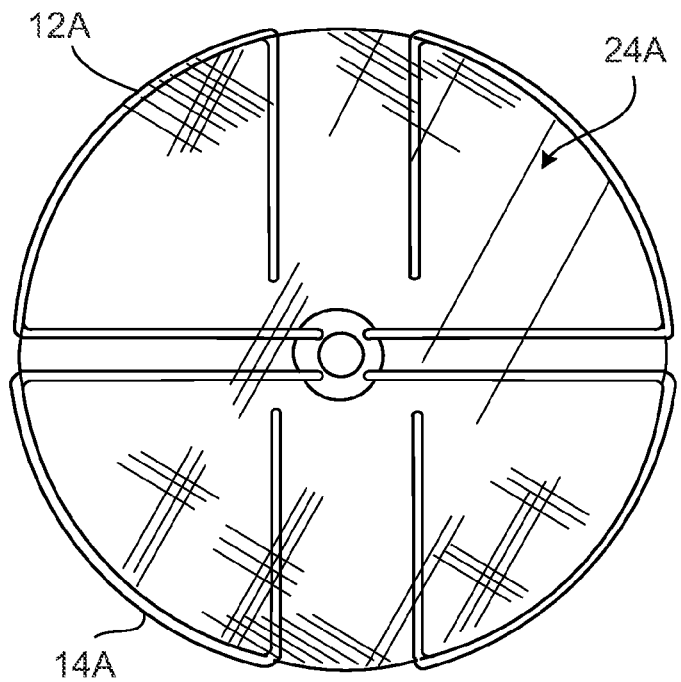
FIG. 7 is a top plan view of the occluder device of FIG. 6.

Coverings 24A and 24B:

According to some embodiments of the present invention, the distal disc 16 and/or proximal disc 18 may include membranous coverings 24A and 24B, illustrated in FIGS. 6 and 7. The membranous coverings 24A and 24B ensure more complete coverage of aperture 6 and promote encapsulation and endothelialization of tissue, thereby further encouraging anatomical closure of the tissue and improving closure rate. The coverings 24A and 24B also help stabilize the occluder device 10.

The membranous coverings 24A and 24B may be formed of any flexible, biocompatible material capable of promoting tissue growth and/or act as a sealant, including but not limited to DACRON®, polyester fabrics, Teflon-based materials, ePTFE, polyurethanes, metallic materials, polyvinyl alcohol (PVA), extracellular matrix (ECM) or other bioengineered materials, synthetic bioabsorbable polymeric materials, other natural materials (e.g. collagen), or combinations of the foregoing materials. For example, the membranous coverings 24A and 24B may be formed of a thin metallic film or foil, e.g. a nitinol film or foil, as described in U.S. Pat. No. 7,335,426 (the entirety of which is incorporated herein by reference). The preferred material is Poly(tetrafluoroethene) (ePTFE), as it combines several important features such as thickness and the ability to stretch. Loops may also be stitched to the membranous coverings 24A and 24B to securely fasten the coverings to occluder 10. The coverings may alternatively be glued, welded or otherwise attached to the occluder 10 via the wires 12, 14.

Size:

As illustrated in FIGS. 2-7, the diameters of the distal disc 16 and proximal disc 18 are generally 5-8 mm larger than the diameter of the connecting waist 20. For example, if the diameter of the connecting waist 20 is 4 mm, the diameters of the discs 16,18 are generally about 9 mm each. Because of the flexibility in the waist 20, a 12 mm waist device will be able to be placed in a 6 mm to 12 mm defect. For larger waists 20 or larger devices, the diameter of the disc size will increase proportionately.

It is within the scope of the present invention to envision occluder devices available in 7 or more sizes, specifically waist size having the following diameters for different-sized apertures 6: 6 mm, 12 mm, 18 mm, 24 mm, 30 mm, 36 mm, and 42 mm.

Operation:

In general, the occluder 10 may be inserted into an aperture 6 to prevent the flow of blood therethrough. As a non-limiting example, the occluder 10 may extend through a PFO 6A or an ASD 6B such that the distal disc 16 is located in the left atrium 3 and the proximal disc 18 is located in the right atrium 2 (as shown in the heart 1 in FIG. 1). The closure of apertures in these and other tissues, as well as other types of apertures, will become apparent as described below.

Figure 8:
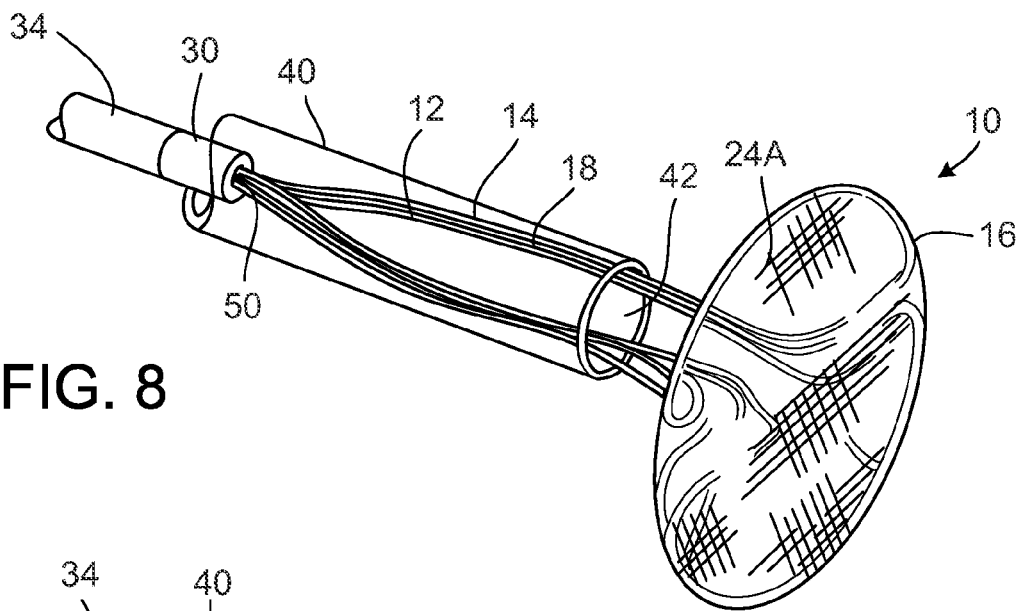
FIG. 8 is a perspective view of the occluder device first emerging from the catheter.
Figure 9:
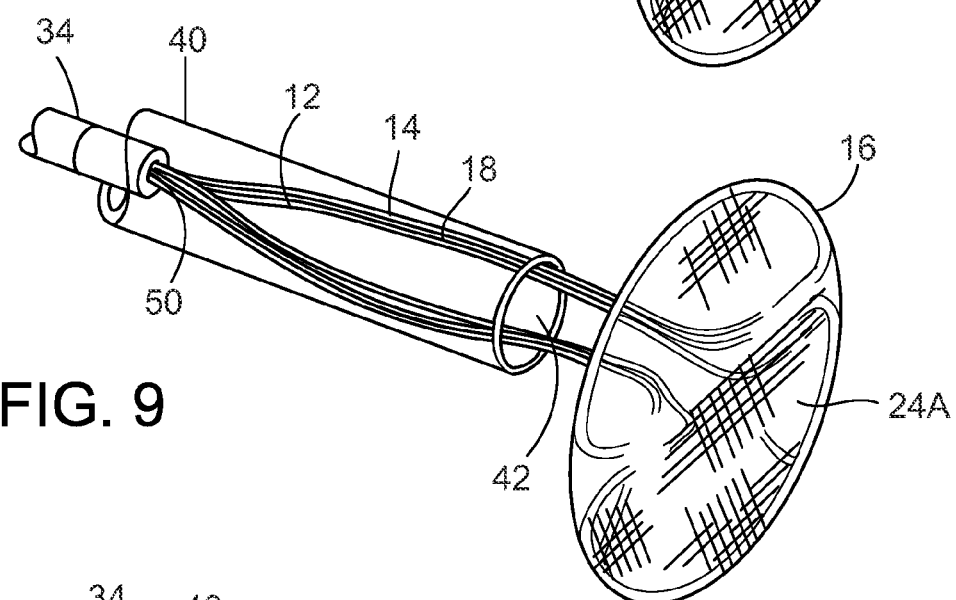
FIG. 9 is a perspective view of the occluder device halfway emerged from the catheter.
Figure 10:
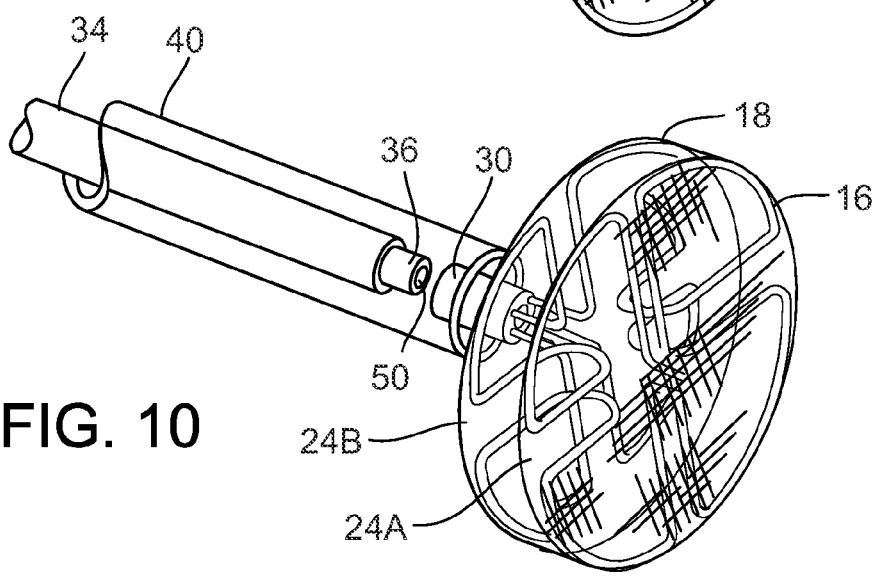
FIG. 10 is a perspective view of the occluder device fully emerged from the catheter and separated from the deployment cable.

Referring now to FIGS. 8-10, the occluder device 10 is attached to a deployment cable 34 which is removably attached to the occluder device 10 at the hub 30. As illustrated in FIG. 10, one method of releasably attaching the deployment cable 34 to the hub 30 is by threaded engagement utilizing a screw end 36 which engages unseen female threads within the hub 30. Other known means of attachment can be used to releasably connect the deployment cable 34 to the hub 30.

When the deployment cable 34 is engaged with the hub 30, as illustrated in FIGS. 8 and 9, the occluder device 10 is initially housed within a flexible delivery catheter 40 having an open channel 42. Reference is made to FIG. 8 which illustrates the occluder device 10 in which the distal disc 16 is expanded, due to the memory expansion of the wires 12 and 14, and housed within the open channel 42 of the delivery catheter 40. During the initial stages of placement of the occluder device 10, both the distal disc 16 and proximal disc 18, as well as the coverings 24A and 24B, are housed within the open channel 42 of the delivery catheter 40. In this manner, the catheter 40 is fed into the blood vessel through an already placed sheath and advanced via the blood vessel system to a defect in the heart.

Once the delivery catheter 40 traverses the aperture that needs to be occluded, e.g., a hole in the heart, the device 10 will be partially advanced from the catheter 40 as illustrated in FIG. 8. As the device 10 leaves the catheter 40, the distal disc 16, which includes the covering 24A, begins to expand on the distal side of the aperture. Due to the memory capabilities of the wires 12 and 14, the occluder device 10 begins to return to its normal shape such that the distal disc 16 expands on the distal side of the aperture in the heart. Once the distal disc 16 is completely out of the catheter opening 42, as shown in FIG. 9, it 16 and the attached covering 24A become fully expanded. The catheter 40 is further withdrawn to expose the waist 20 which then begins to emerge and expand due to the memory shape of the wires 12 and 14. Advantageously, the waist 20 is designed to expand such that each of the wires forming the waist 20 are urged against the aperture in the heart causing a custom fit device of the occluder 10 within the aperture. As the catheter 40 is further withdrawn, the proximal disc 18 and the covering 24B begin their process of expansion on the proximal side of the aperture. When the proximal disc 18 is fully delivered from the catheter 40, it will expand and effectively form a seal over the aperture. The distal disc 16 and proximal disc 18 are secured in place by the action of the wires in the waist 20 urging against the aperture. At this stage, as shown in FIG. 10, the deployment cable 34 is removed from the hub 30 and the catheter 40 and the deployment cable 34 are removed from the body. The occluder device 10 is left in the heart at the region of the aperture. Over several months, skin tissue and other membranous structures will bind to the occluder device 10 thereby permanently locking the occluder device 10 to the specific area in the heart.

The two wires 12, 14 function to form round discs 16, 18 on each side of the tissue. The discs 16, 18 maintain the circular shape because of the memory capability of the wires 12, 14. The coverings 24A, 24B will stabilize the discs and will act to completely occlude the defect.

The wires 12, 14 at the waist portions 12C, 14C will be separated enough at the waist 20 to make the occluder device 10 self-centering. Due to the conformity of this design, the occluder device 10 should self-center within commonly (round, oval) shaped septal defects, as the waist 20 can adjust to any type of opening.

If a larger-diameter waist 20 is required, the waist 20 has the capability to expand (only if needed) to a larger size with the help of a balloon. In this manner, a center channel 50 extends through the deployment cable 34, the hub 30, and the screw end 36. A balloon (not shown) is urged through the center channel 50 after the occluder device has been removed from the catheter 40 and expanded, and preferably before the hub 30 has been attached from the deployment cable 34. The balloon is placed within the waist 20 and expanded. The waist 20 is dilatable, i.e., expandable, when gentle pressure of the balloon is applied. The dilation will expand the waist portions 12C, 14C. Once the desired diameter is reached, the balloon is deflated and removed by withdrawal through the center channel 50. Once the occluder device 10 appears stable, the device 10 is separated from the deployment cable 34 as discussed above. In the majority of cases, balloon dilation will not be required.

Figure 11:
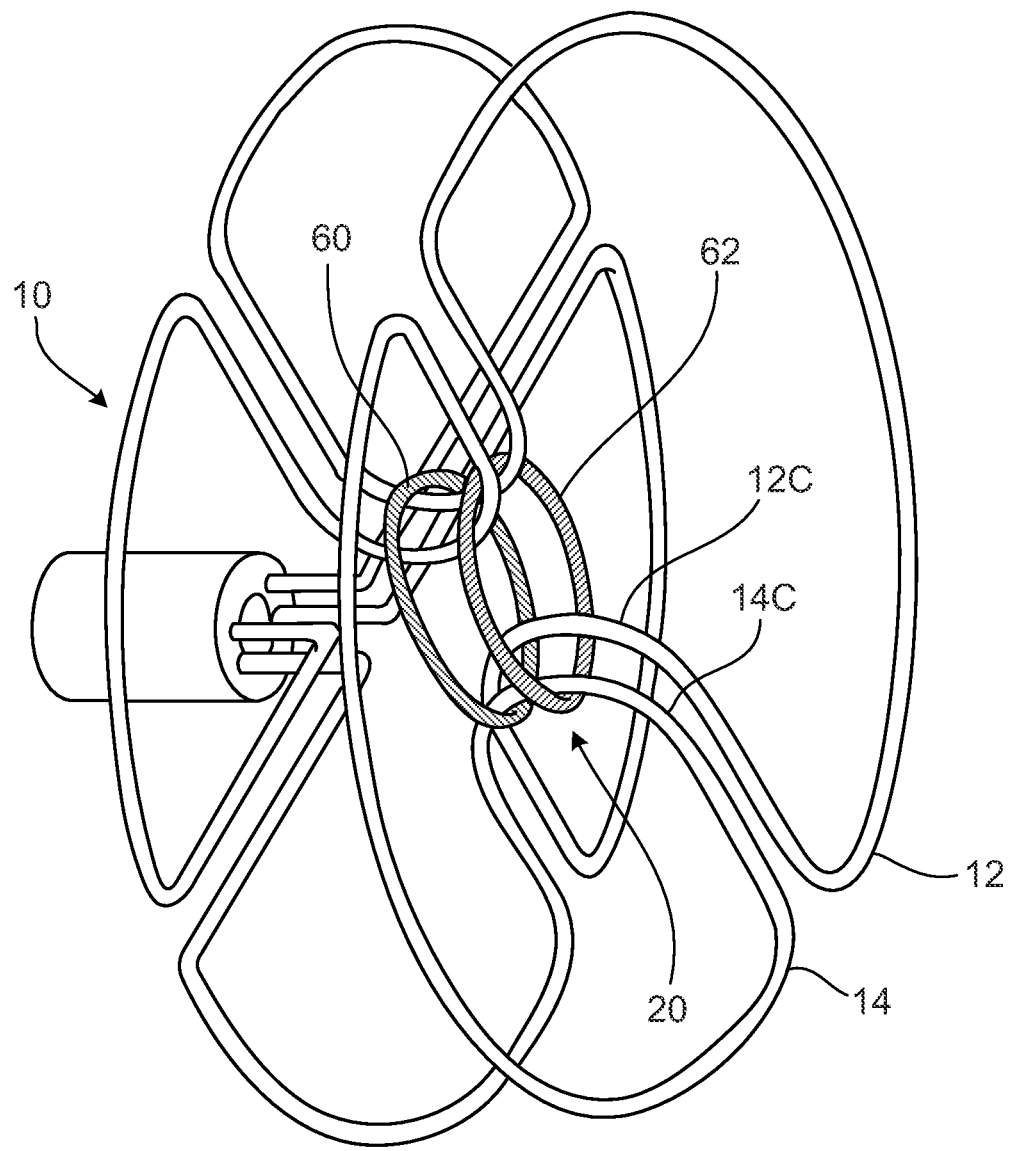
FIG. 11 is a perspective view of the occluder device of the present invention illustrating restriction wires encircling the waist of the occluder device.

Restriction Wires 60, 62 (FIG. 11):

In order to increase stability in the occluder device 10 and to avoid significant crimping of the waist 20 or the proximal or distal discs 18, 16, the waist 20 can be encircled by one or more restriction wires 60, 62 as illustrated in FIG. 11. The restriction wires 60, 62 can be made of the same wire material as the wires 12 and 14, or they may be of a different material, such as plastic wire, fish line, etc. The restriction wires 60, 62 may be welded or otherwise connected to the waist portions 12C, 14C. The purpose of the restriction wires 60 or 62 is also to restrict the circumference of the waist 20 if necessary. Although one restriction wire 60 is generally suitable, a second restriction wire 62 can also be incorporated to further improve stability.

Alternative Embodiments

Reference is now made to FIGS. 12-15 for alternative embodiments of the occluder device 10 of the present invention. Unless otherwise noted, the same reference numbers will be applied to similar structures in each embodiment.

Figure 12A:
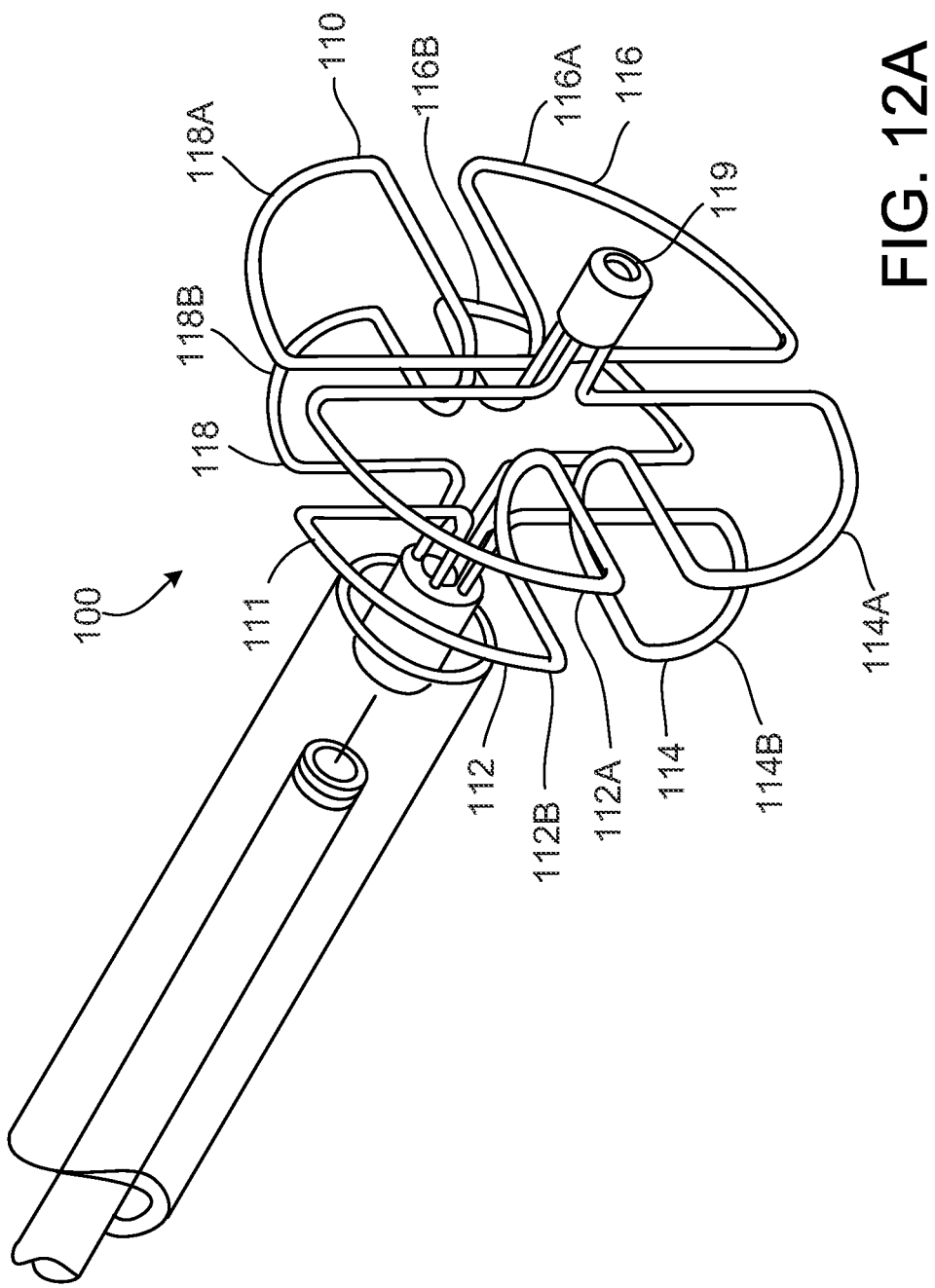
FIG. 12A is a perspective view of a first alternative embodiment of the occluder device of the present invention.
Figure 12B:
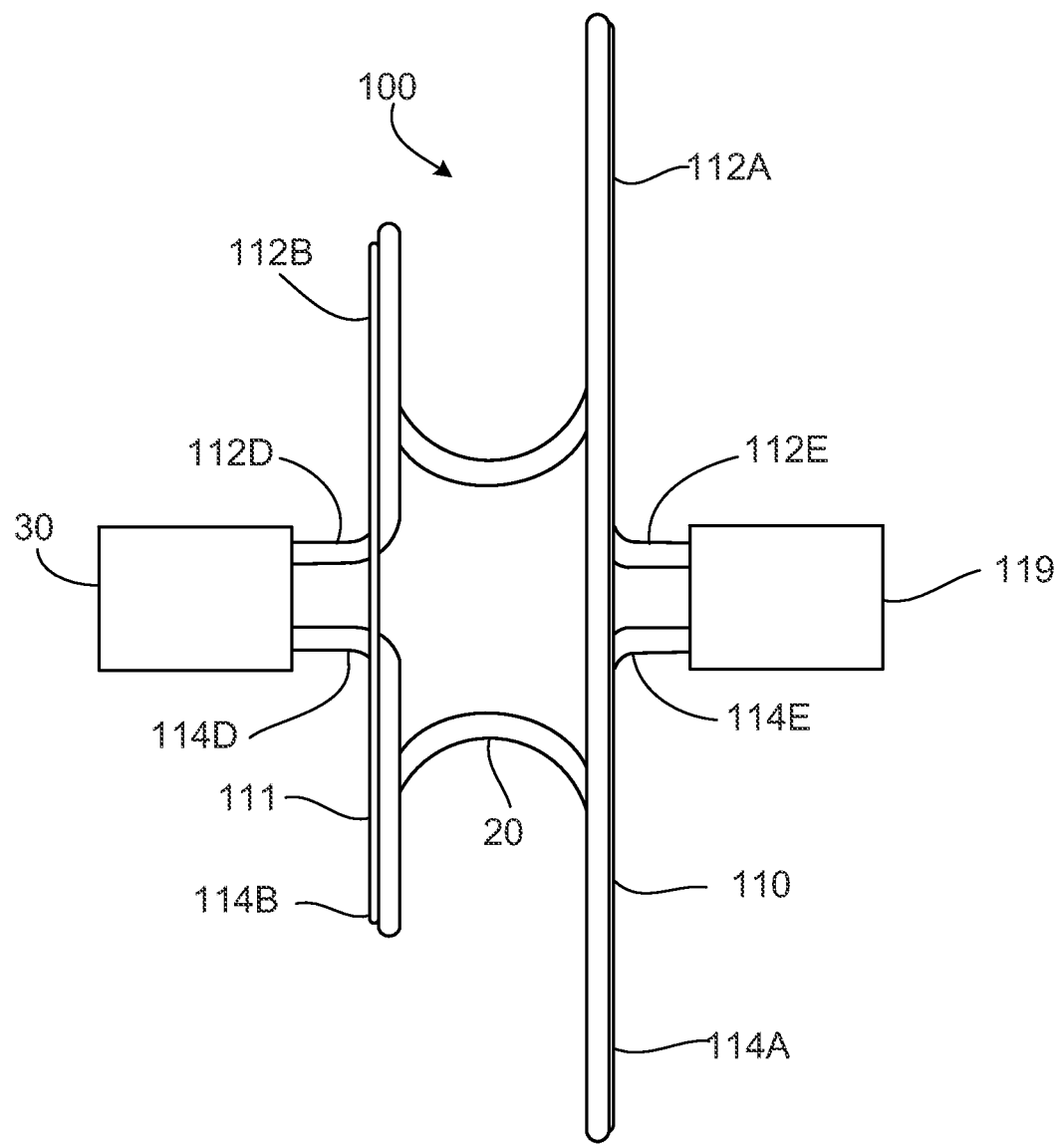
FIG. 12B is a side plan view of the first alternative embodiment of the occluder device of the present invention as shown in FIG. 12A.

Reference is made to FIGS. 12A and 12B for an alternative embodiment of the occluder device (labeled as occluder device 100 in FIGS. 12A and 12B). The occluder device 100 in this embodiment is designed for PDA procedures. This embodiment is similar to previously described embodiments except that it is comprised of four wires 112, 114, 116, 118 rather than two wires. In this case, each wire forms a mirror image of each of its neighboring wires. For example, wire 112 mirrors wire 114 as well as wire 118, etc. Each of the four wires 112, 114, 116, 118 forms a proximal quarter-disc 112B, 114B, 116B, 118B and a distal quarter-disc 112A, 114A, 116A, 118A. The proximal quarter-discs 112B, 114B, 116B, 118B together form a proximal disc 111 in a "four-leaf clover" configuration, and the distal quarter-discs 112A, 114A, 116A, 118A together form a distal disc 110 also in a "four-leaf clover" configuration. This embodiment also differs from previously-described embodiments in that the waist 20 is comprised of a single portion of each of the four wires 112, 114, 116, 118. This embodiment further differs from previously-described embodiments in that it comprises a second hub 119 with a screw mechanism. The second hub 119 connects to the distal disc 110 by distal ends 112E, 114E (116E, 118E behind 112E, 114E in FIG. 12B) of each of the four wires 112, 114, 116, 118, just as proximal ends 112D, 114D (116D, 118D behind 112D, 114D in FIG. 12B) connect to the proximal hub 30. The wires 112, 114, 116, 118 may be connected to the hubs 30, 119 by welding or other means known in the art. The length of the waist 20 will be anywhere from 4-8 mm. In addition, the distal disc 110 is typically 4-8 mm larger than the waist 20. However, the proximal disc 111 is generally 1-3 mm, preferably 2 mm, larger than the waist 20 diameter. Hence, the diameter of the distal disc 110 is larger than the diameter of the proximal disc 111.

Figure 13:
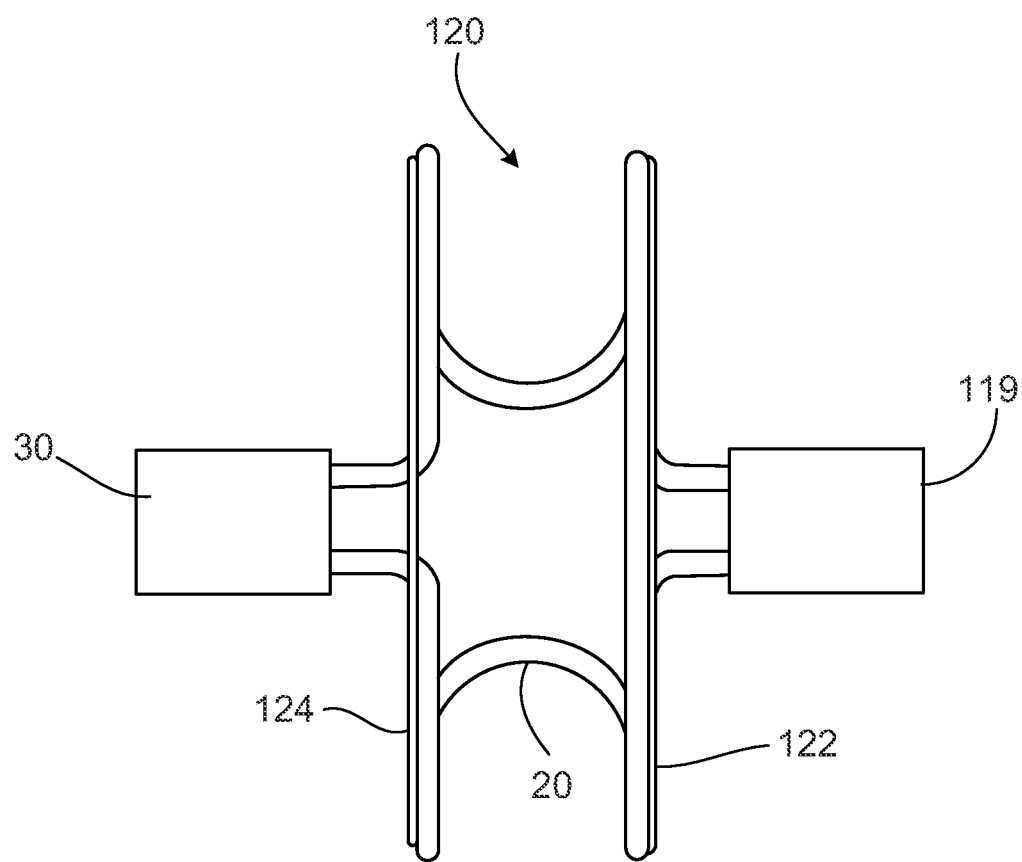
FIG. 13 is a side plan view of a second alternative embodiment of the occluder device of the present invention.

Reference is now made to FIG. 13 for a second alternative embodiment of the occluder device 120. This embodiment, like the embodiment shown in FIGS. 12A and 12B, uses four wires 112, 114, 116, 118 and two hubs 30, 119. It is designed to close apertures in large arteries and veins. In occluder device 120, the distal and proximal discs 122 and 124 are modified so that they are compatible with closure of veins and arteries. For this use, the connecting waist 20 is equivalent or near equivalent to the diameter of each of the discs 122, 124. The diameter of the waist 20 will be 1 mm smaller than the discs 122, 124. The length of the waist will be 4-8 mm. This embodiment can be used in the closure of coronary artery fistulas, arteriovenous fistulas, and arteriovenous malformations.

Figure 14:
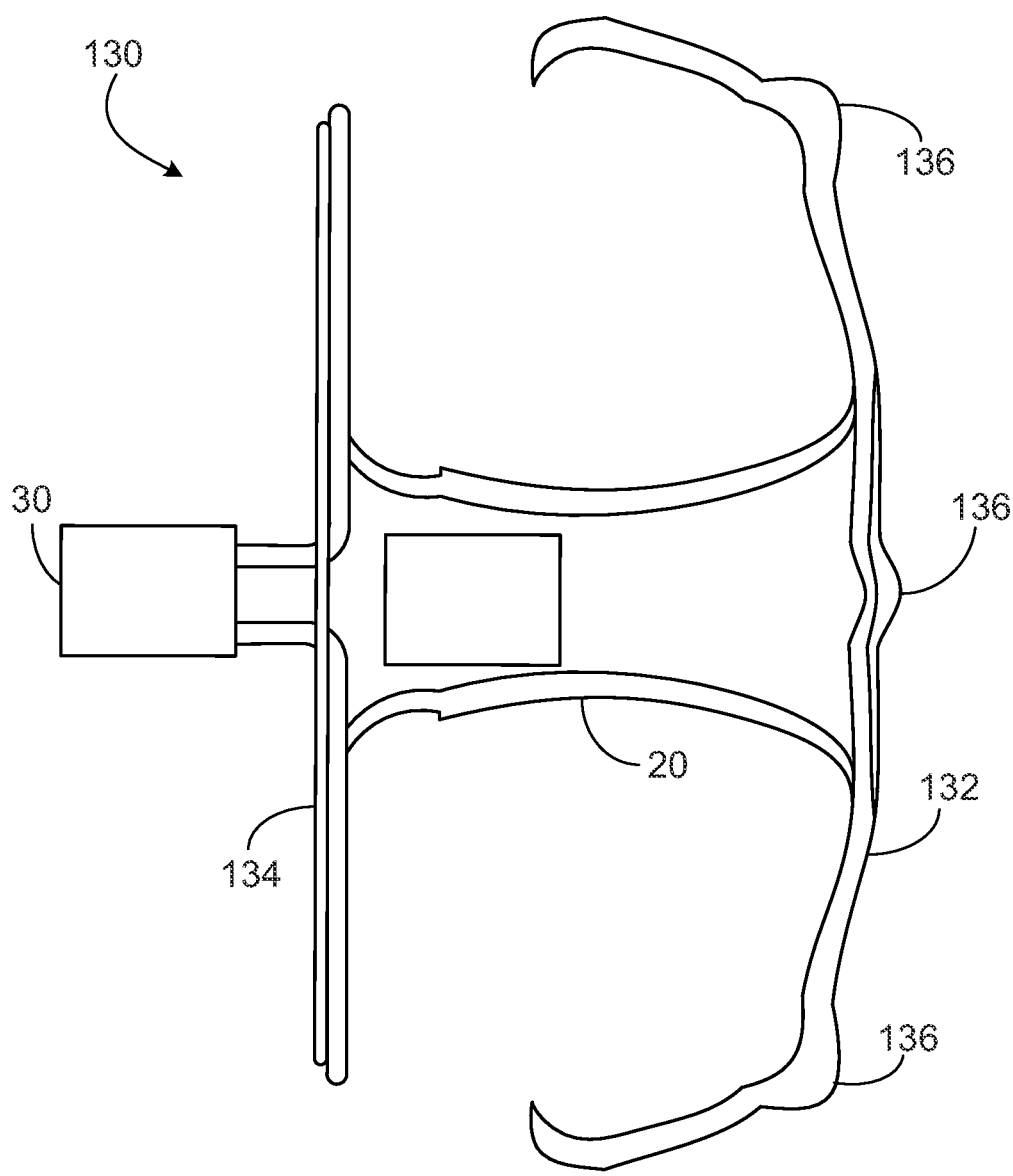
FIG. 14 is a side plan view of a third alternative embodiment of the occluder device of the present invention.

Reference is made to FIG. 14 for a third alternative embodiment of the occluder device 130. The importance of the occluder device 130 will be in the closure of the left atrial appendage. The device 130 is modified to conform to the atrial appendage anatomy. The distal disc 132 is modified so that the device 130 is not extruded out with the heartbeats. For the left atrial appendage occluder device 130, the memory wire structure of the distal disc 132 is woven to form anywhere from 2 to 8 protuberances or hooks 136. Upon inserting the device 10 in an aperture in the left atrial appendage of the heart, the hooks 136 grip the outer portion of the left atrium heart tissue and thereby assist in keeping the device 130 from extruding out of the left atrial appendage with contraction of the heart. The proximal disc 134 is typically flat and similar to the disc formed by the proximal discs 18 in FIGS. 2-7. The proximal disc 134 abuts the inner atrial wall of the heart. Typically, the waist 20 will be about 4-8 mm in diameter. The length of the waist may range from 4 to 16 mm.

Figure 15:
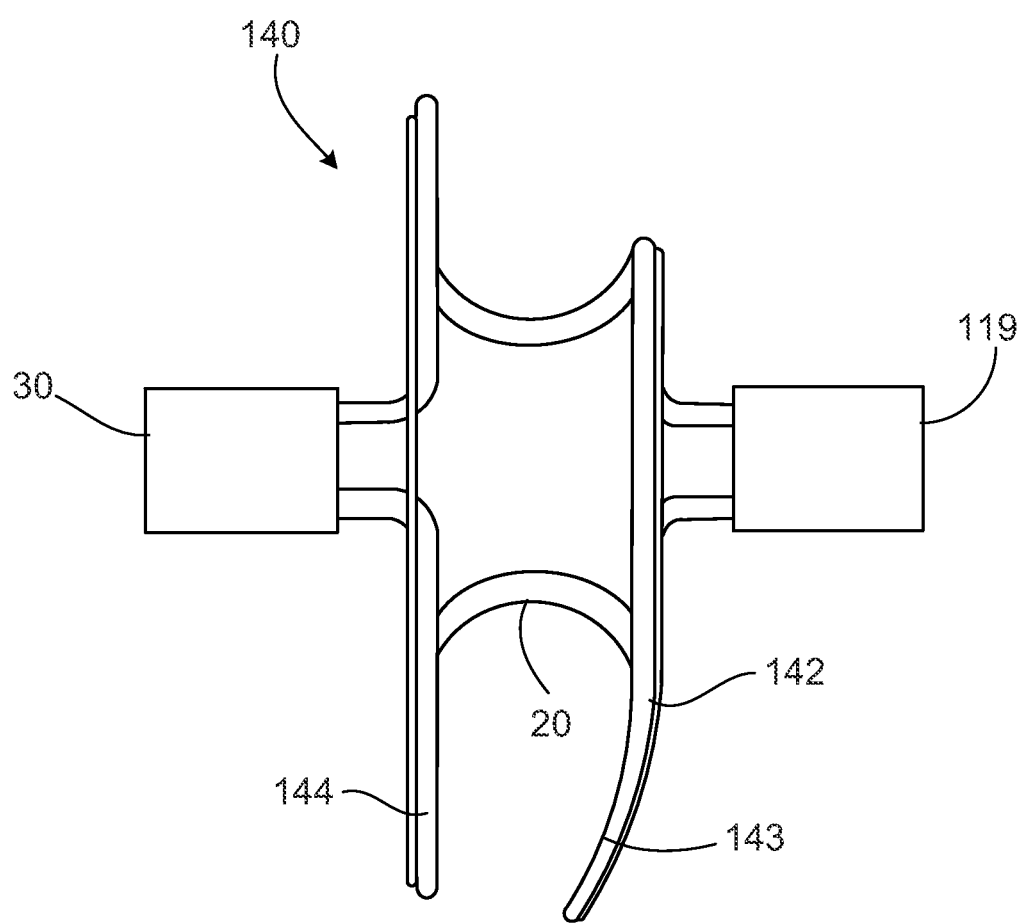
FIG. 15 is a side plan view of a fourth alternative embodiment of the occluder device of the present invention.

Reference is made to FIG. 15 for a fourth alternative embodiment of the occluder device 140. Occluder device 140 is intended to occlude perimembranous ventricular septal ("PVS") defects. This embodiment, like the embodiment shown in FIGS. 12A and 12B, uses four wires 112, 114, 116, 118 and two hubs 30, 119. The occluder device 140 is different from other embodiments in that two of the four wires form truncated distal-quarter discs, with the effect that the distal disc 142 substantially misses half of the disc. Therefore, the device 140 has approximately 1.5 discs as opposed to two discs. The half distal disc 142 is also significantly longer than the proximal disc 144. Typically, the distal disc 142 will be 6-8 mm in diameter. In addition, the distal disc 142 converges or curves inwards at 143, i.e., it is angled to contact the ventricular septum when the device 140 is inserted in the PVS defect. (See below for details.) The lower edge of the proximal disc (opposite to the long distal disc) will be 3-4 mm larger than the waist, and the other half of the proximal disc will be 2-3 mm larger than the waist. The discs can also be modified to be of different shapes in the same device. Alternatively, the disc angle may be created by a straight distal disc 142 angled with respect to the plane perpendicular to the waist 20 in a slant fashion.

Figure 16:
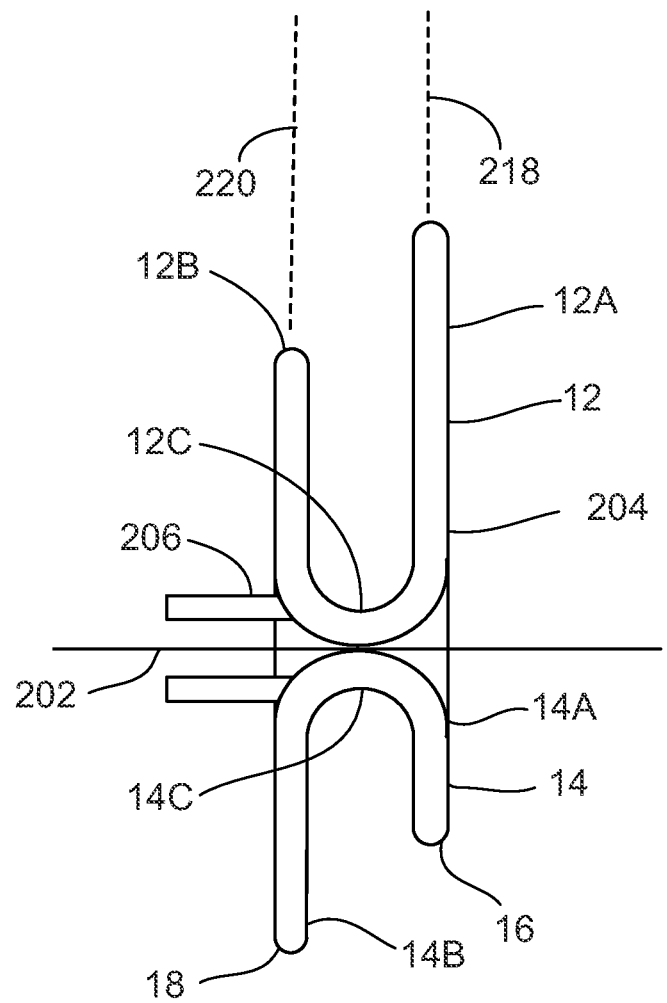
FIG. 16 is a side view of another exemplary alternative embodiment of the occluder device.

With reference to FIGS. 16-22, various additional exemplary alternative embodiments are provided with respect to the occluder device and/or components thereof. With reference to FIG. 16, certain embodiments of the occluder device 10 may have one or more plates 16, 18 and/or geometric forms 12A, 12B, 14A, 14B of different sizes and/or configurations as compared with the embodiment described above in connection with FIG. 2. For example, the distal (or first) plate 16 and the proximal (or second) plate 18 may be offset with respect to the hub 30, and/or one side of a plate 16, 18 may be relatively higher or farther from the hub 30 than the other, for example via an oblique shift. In the particular embodiment of FIG. 16, a center 202 of the hub 30 is not aligned with (and, rather, is offset against) a center 204 of the first plate 16, but is aligned with a center 206 of the second plate 18. In another embodiment, the distal plate 16 and the proximal plate 18 are of equal size, yet offset from each other via a shift in opposite directions from the hub.

In certain embodiments, the first and second plates 16, 18 are configured such that a first segment formed from a first portion of the first wire 12 (for example, corresponding to form 12B of FIG. 16) has a first length, a second segment formed from a first portion of the second wire 14 (for example, corresponding to form 14A of FIG. 16) has a second length, a third segment formed for a second portion of the first wire 12 (for example, corresponding to form 12A of FIG. 16) has a third length, and a fourth segment formed for a second portion of the second wire 14 (for example, corresponding to form 14B of FIG. 16) has a fourth length. The second length is substantially equal to the first length. The third length is greater than the first length. The fourth length is substantially equal to the third length.

The semi-circle or half-disc 12A of the first wire 12 (also referenced above as the first geometric form 12A of the first wire 12) may differ in size (for example, having a larger radius and therefore a larger surface area) from the semi-circle or half-disc 14A of the second wire 14 (also referenced above as the first geometric form 14A of the second wire 14). In certain other embodiments, the semi-circle or half-disc 12A of the first wire 12 and the semi-circle or half-disc 14A of the second wire 14 may be of the same size same as one another, but may collectively form a distal plate 16 that differs in size from the proximal plate 18. In one such embodiment, the distal plate 16 is smaller in surface area than the proximal plate 18.

For example, the distal plate 16 may be of the same size as in FIG. 2, while the proximal plate 18 is larger in surface area than depicted in FIG. 2. This may occur, by way of example, when certain of the proximal quarter-circles of the second geometric forms 12B, 14B are larger in surface area than depicted in FIG. 2. Certain proximal quarter-circles of the second geometric forms 12B, 14B may be larger in surface area than other, adjacent quarter-circles of the second geometric forms 12B, 14B. Such differing sizes of the proximal quarter-circles of the second geometric forms 12B, 14B may be present regardless of the relative sizes of the distal and proximal plates 16, 18.

Figure 17:
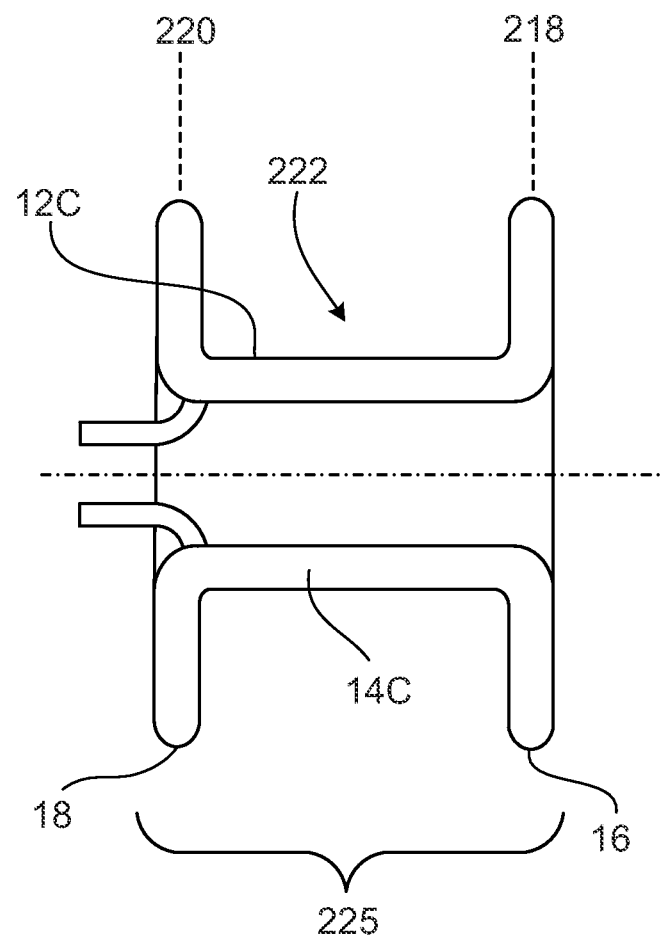
FIG. 17 is a side view of another exemplary alternative embodiment of the occluder device.

FIG. 17 depicts an embodiment of an occluder device contemplated herein with a wider waist 20. In one exemplary embodiment, the first plate 16 and the second plate 18 are disposed further apart as compared with the example of FIG. 2, so that a total length 225 of the waist 20 is greater than eight millimeters. Preferably, in this embodiment, the length 225 of the waist 20 is greater than eight millimeters and less than or equal to ten millimeters. In one such example, a straight-line distance between the first plane 218 and the second plane 220 of FIG. 2 is greater than eight millimeters, and is preferably also less than or equal to ten millimeters.

Figure 18:
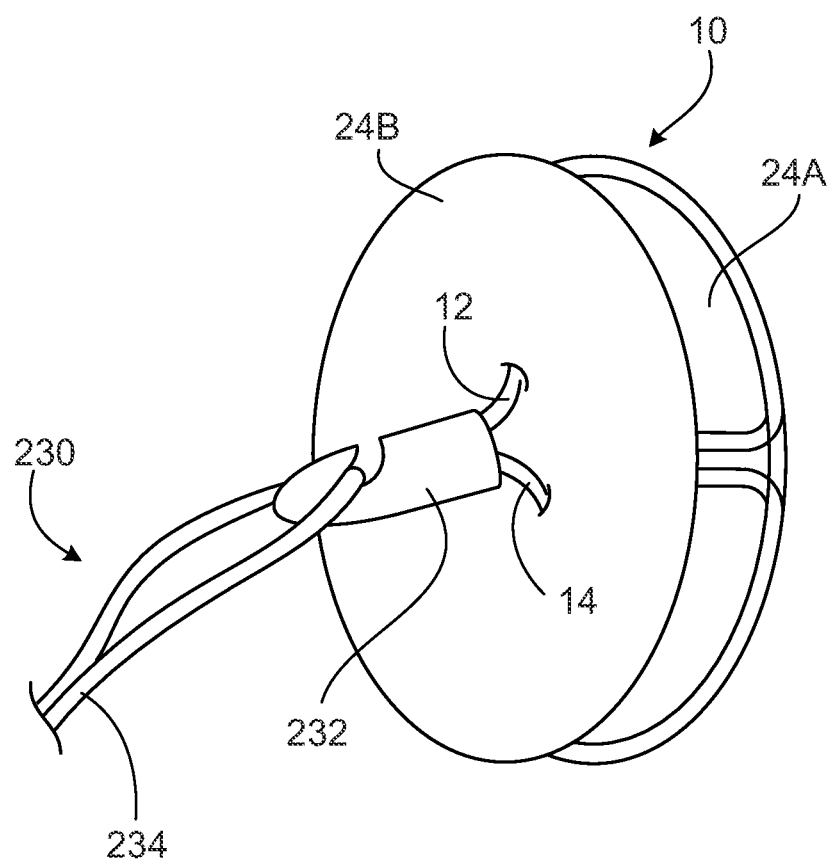
FIG. 18 is a perspective view of another exemplary alternative embodiment of the occluder device.

FIG. 18 depicts an embodiment of an occluder device contemplated herein with a hook engagement system 230. The hook engagement system 230 comprises a hook 232 and a lanyard 234 coupled thereto. The hook 232 is connected to the first plate 16 or the second plate 18 (and to the first and/or second wires 12, 14 thereof) described above, preferably proximate one of the coverings 24A, 24B. The hook engagement system 230 is configured for engagement with a positioning system (not depicted). In one embodiment, the hook engagement system 230 is used to remove the occluder device 10 from the heart. In this regard, a loop of the lanyard 234 is positioned onto the hook 232, and the lanyard 234 is pulled in the direction away from the heart, thus pulling the occluder device 10 through the heart aperture and through the body. In another embodiment, the positioning system comprises a deployment system for deploying the occluder device 10, for example by grasping the hook 232 for movement of the occluder device 10 into a human heart in a desired position proximate an aperture. In a further embodiment, the positioning system comprises a repositioning system for repositioning the occluder device 10, for example by grasping the hook 232 for adjusting the position of the occluder device 10 for more ideal placement of the occluder device 10 proximate an aperture. In certain embodiments, the lanyard (and/or another connection feature) is part of the positioning system, and the hook may exist separately from the occluder device 10. The hook 232 is preferably used in connection with a screw device for further engagement with the positioning system, such as a screw and nut system used in conjunction with FIGS. 8-10 described above. For example, the hook 232 may be positioned internal to a screw and nut system during placement of the device. Alternatively, the hook 232 may be used in connection with a thread cord through an eyelet or an opening, so that the cord would need to be pulled in order to lose the connection with the occluder device 10. In addition, such a cord may be used for retrieval of the occluder device 10, for example by including multiple lumens, preferably with an opening or slit, as part of a catheter delivery system.

Figure 19:
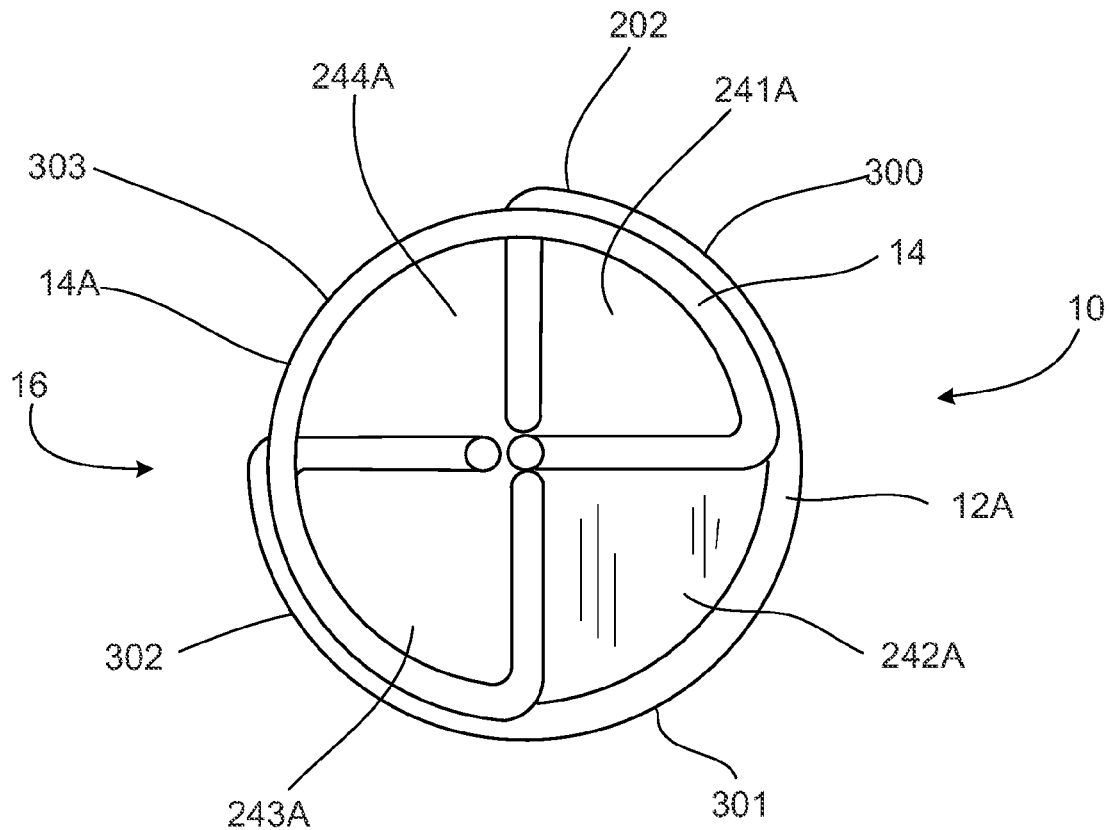
FIG. 19 is a plan view of another exemplary alternative embodiment of the occluder device, depicted with reference to planar quadrants in FIG. 19A.
Figure 19A:
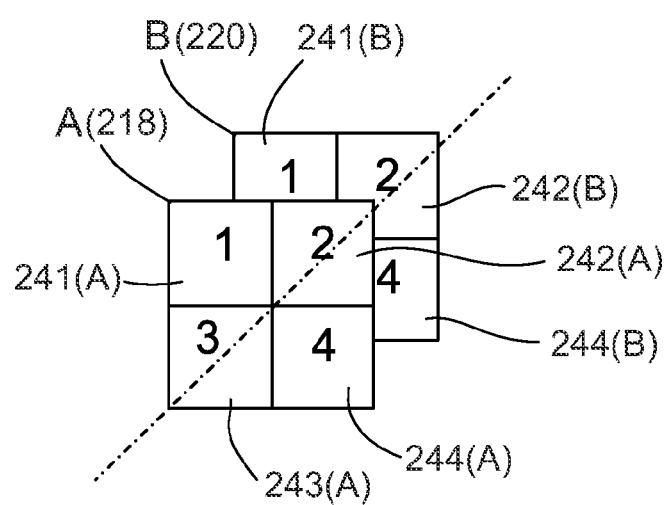

With reference to FIGS. 19 and 19A, an embodiment of an occluder device contemplated herein is depicted with overlapping wires at least at one plate. Overlapping wires add additional strength and rigidity to the plate of the occluder device. Specifically, the first geometric form 12A of the first wire 12 overlaps at least a portion of one region (for example, at least a portion of a common spatial quadrant, half-plane, and/or quartile) in common with the first geometric form 14A of the second wire 14 within the first plate 16. Alternatively, or in addition, the second geometric form 12B (not shown) of the first wire 12 overlaps at least a portion of one region (for example, at least a portion of a common spatial quadrant, half-plane, and/or quartile) in common with the second geometric form 14B (not shown) of the second wire 14 within the second plate 18 (not shown).

In a preferred embodiment, as illustrated in FIG. 19, the first geometric form 12A of the first wire 12 occupies at least three spatial quadrants 300, 301, and 302, two of which (namely, spatial quadrants 300 and 302) are shared in their entireties with the first geometric form 14A of the second wire 14. Likewise, the first geometric form 14A of the second wire 14 occupies at least three spatial quadrants 302, 303, and 300, two of which (namely, spatial quadrants 300 and 302) are shared in their entireties with the first geometric form 12A of the first wire 12. Similarly, the second geometric form 12B of the first wire 12 (not depicted in FIG. 19) occupies at least three spatial quadrants, two of which are shared in their entireties with the second geometric form 14B of the second wire 14 (not depicted in FIG. 19). Likewise, the second geometric form 14B of the second wire 14 occupies at least three spatial quadrants, two of which are shared in their entireties with the second geometric form 12B of the first wire 12.

FIG. 19A depicts an exemplary classification of planar quadrants for the first and second planes 218, 220 of FIG. 2 for reference with respect to the embodiment of FIG. 19. One skilled in the art will recognize that less or more than four quadrants can be utilized. With reference to FIG. 19A, the first plane 218 of FIG. 2 has a first quadrant 241(A), a second quadrant 242(A) that is adjacent to the first quadrant 241(A), a third quadrant 243(A) that is below the first quadrant 241(A), and a fourth quadrant 244(A) that is below the second quadrant 242(A) and adjacent to the third quadrant 243(A). The second plane 220 of FIG. 2 has a first quadrant 241(B), a second quadrant 242(B) that is adjacent to the first quadrant 241(B), a third quadrant 243(B) that is below the first quadrant 241(B), and a fourth quadrant 244(B) that is below the second quadrant 242(B) and adjacent to the third quadrant 243(B). The first quadrant 241(A) of the first plane 218 is closer to the first quadrant 241(B) of the second plane 220 than to the second, third, or fourth quadrants 242(B), 243(B), 244(B) of the second plane 220. The second quadrant 242(A) of the first plane 218 is closer to the second quadrant 242(B) of the second plane 220 than to the first, third, or fourth quadrants 241(B), 243(B), 244(B) of the second plane 220. The third quadrant 243(A) of the first plane 218 is closer to the third quadrant 243(B) of the second plane 220 than to the first, second, or fourth quadrants 241(B), 242(B), 244(B) of the second plane 220. The fourth quadrant 244(A) of the first plane 218 is closer to the fourth quadrant 244(B) of the second plane 220 than to the first, second, or third quadrants 241(B), 242(B), 243(B) of the second plane 220.

With reference to the spatial quadrants set forth in FIG. 19A, in one preferred embodiment of FIG. 19, the first geometric form 12A of the first wire 12 extends through the first, second, and third quadrants 241(A), 242(A), 243(A) of the first plane 218. The first geometric form 14A of the second wire 14 extends through the first, third, and fourth quadrants 241(A), 243(A), and 244(A) of the first plane 218. Accordingly, in this embodiment, the first geometric forms 12A, 14A of the first and second wires 12, 14 share the first and third quadrants 241(A), 243(A) of the first plane 218 in common, for example to provide increased support and/or rigidity for the occluder device 10.

Also in one version of this embodiment of FIG. 19, the second geometric form 12B of the first wire 12 extends through the first, second, and third quadrants 241(B), 242(B), 243(B) of the second plane 220. The second geometric form 14B of the second wire 14 extends through the first, third, and fourth quadrants 241(B), 243(B), 244(B) of the second plane 220. Accordingly, in this version, the second geometric forms 12A, 14A of the first and second wires 12, 14 share the first and third quadrants 241(B), 243(B) of the second plane 220 in common, for example to provide increased support and/or rigidity for the occluder device 10.

However, this may vary in other versions or embodiments. For example, in another version of the embodiment depicted in FIG. 19, the second geometric form 12B of the first wire 12 extends through the third, fourth, and first quadrants 243(B), 244(B), 241(B) of the second plane 220, and the second geometric form 14B of the second wire 14 extends through the first, second, and third quadrants 241(B), 242(B), 243(B) of the second plane 220.

Figure 20:
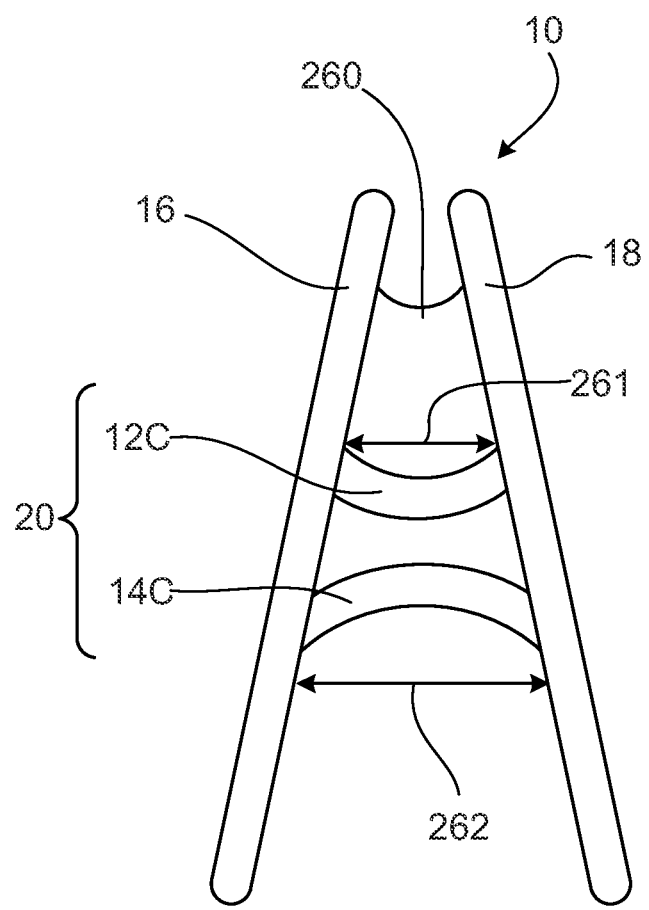
FIG. 20 is a side view of another exemplary alternative embodiment of the occluder device.
Figure 21A:
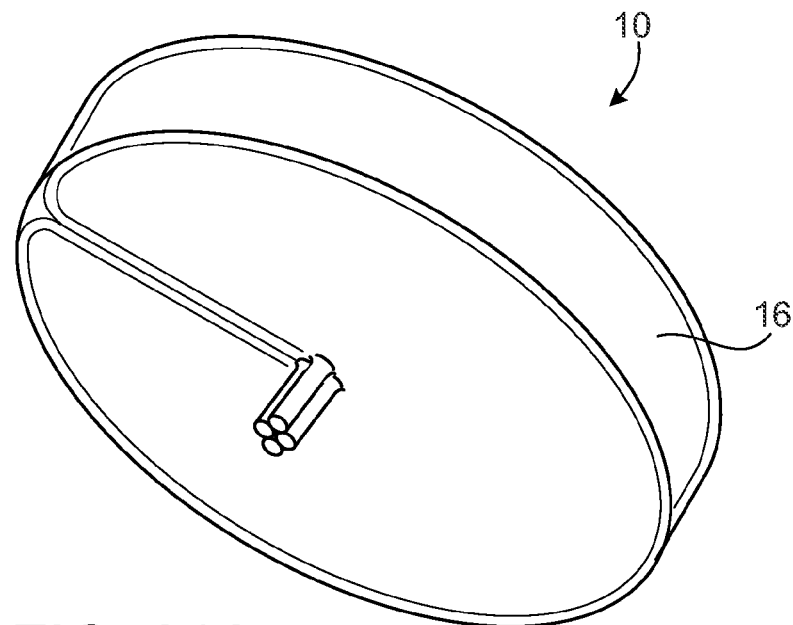
FIG. 21A is a perspective view of another exemplary alternative embodiment of the occluder device.
Figure 21B:
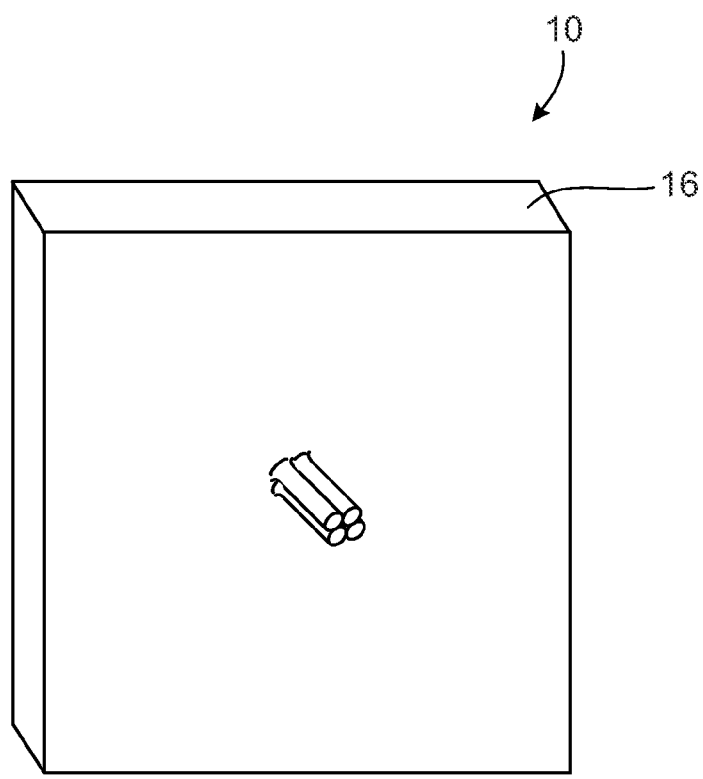
FIG. 21B is a plan view of another exemplary alternative embodiment of the occluder device.
Figure 21C:
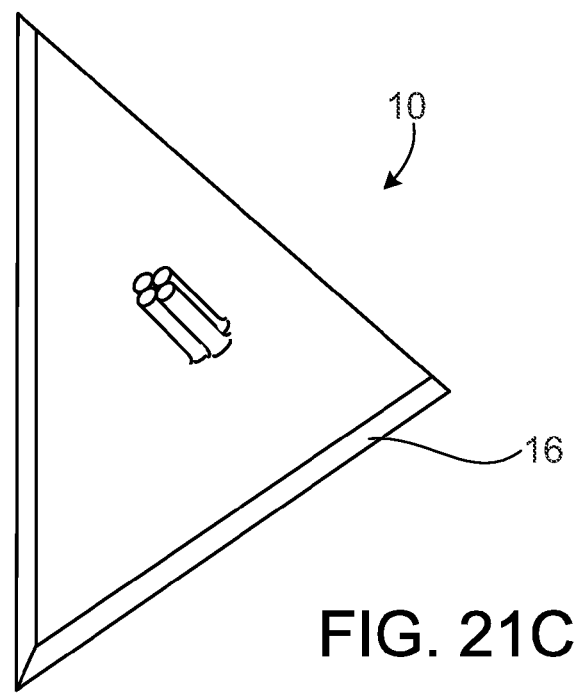
FIG. 21C is a plan view of another exemplary alternative embodiment of the occluder device.
Figure 21D:
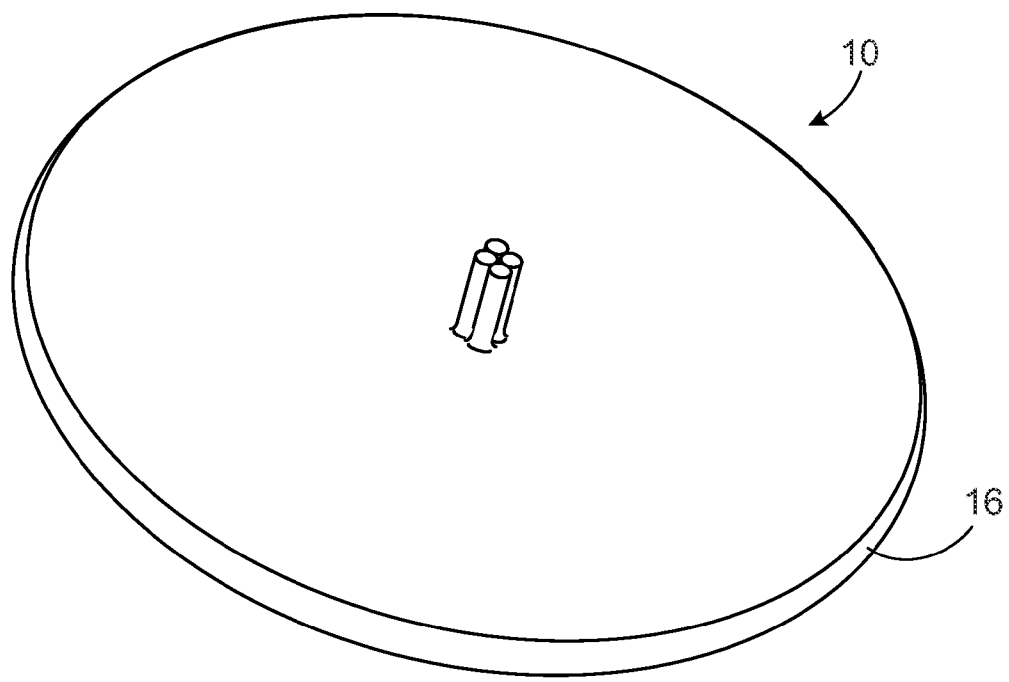
FIG. 21D is a plan view of another exemplary alternative embodiment of the occluder device.
Figure 21E:
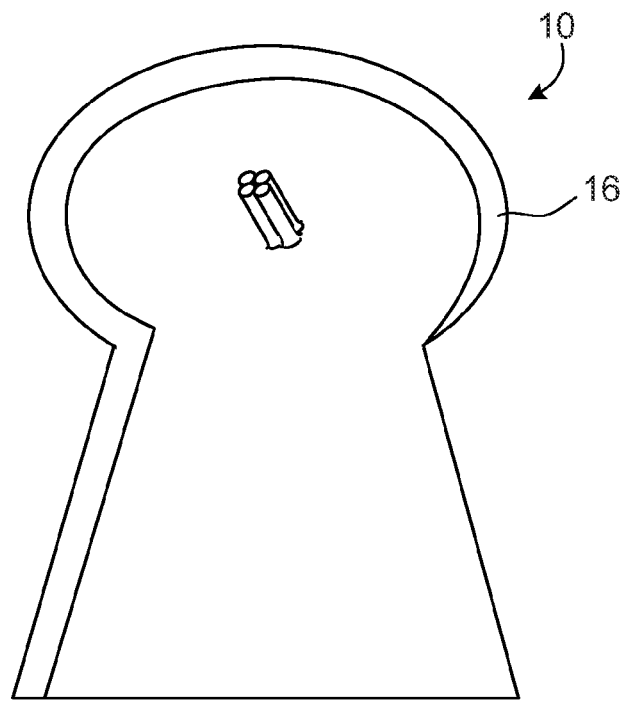
FIG. 21E is a plan view of another exemplary alternative embodiment of the occluder device.

FIG. 20 depicts an embodiment of an occluder device contemplated herein with a clothes-pin shape. In the embodiment of FIG. 20, the first plate 16 and the second plate 18 described above are non-parallel, and form a non-zero angle 260 with respect to one another. The angle 260 is preferably greater than five degrees, is more preferably greater than ten degrees, and is most preferably approximately equal to twenty degrees.

Also in the embodiment of FIG. 20, the waist 20 is configured such that the above-referenced waist components 12C of the first wire 12 and the waist components 14C of the second wire 14 are unequal in size. For example, as shown in FIG. 20, each waist component 12C of the first wire 12 has a first length indicated by double arrow 261, and each waist component 14C of the second wire 14 has a second length indicated by double arrow 262 that is greater than the first length. The length is defined as the distance between the first plate 16 and the second plate 18 taken from a predetermined distance from the occluder device 10's center point. Each waist component 14C of the second wire 14 may also have a greater surface area and radius as compared to respective waist components 12C of the first wire 12. In addition, in the embodiment of FIG. 20, the waist components 12C of the first wire 12 and the waist components 14C of the second wire 14 are preferably configured such that the waist 20 is curved, with a non-zero angle of curvature. The angle of curvature of the waist 20 is preferably greater than five degrees, is more preferably greater than ten degrees, and is most preferably greater than twenty degrees.

FIGS. 21A-21E depict an embodiment of an occluder device contemplated herein in which one or more of the first and second plates 16, 18 are non-circular in their geometric shape(s). In one embodiment of FIG. 21A, at least the first plate 16 has a generally oval shape. In an embodiment of FIG. 21B, at least the first plate 16 has a generally rectangular shape. In an embodiment of FIG. 21C, at least the first plate 16 has a generally triangular shape. In an embodiment of FIG. 21D, at least the first plate 16 has a generally elliptical shape. In an embodiment of FIG. 21E, at least the first plate 16 has a generally keyhole shape. In certain versions, the first plate 16 and/or the second plate 18 have generally the same geometric shapes as one another. In certain other versions, the first plate 16 and/or the second plate 18 differ from one another. The first plate 16 and the second plate 18 may also comprise any number of other different geometric shapes.

Figure 22:
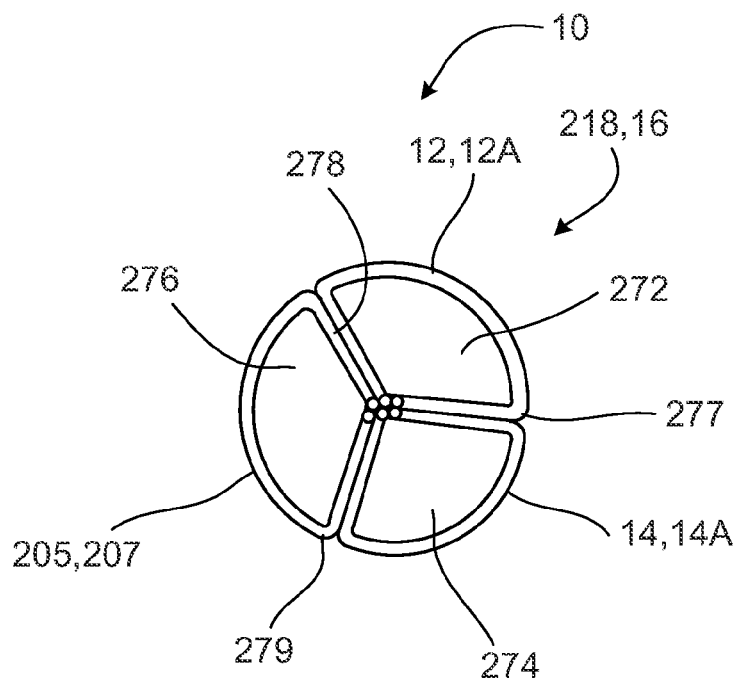
FIG. 22 is a plan view of another exemplary alternative embodiment of the occluder device.

FIG. 22 depicts an embodiment of an occluder device contemplated herein that is formed by more than two wires. Specifically, in the embodiment of FIG. 22, the occluder device 10 has three wires, namely: the first wire 12 and the second wire 14 described above, as well as a third wire 205. In other embodiments, four wires may be utilized. In yet other embodiments, six wires may be utilized. In still other embodiments, the number of wires may differ further.

In the particular embodiment of FIG. 22, the three wires 12, 14, and 205 each form respective, non-overlapping thirds of each plane. Specifically, as depicted in FIG. 22, the first geometric form 12A of the first wire 12 is disposed within and extends through a first region 272 of the first plane 218 described above. The second geometric form 12B of the second wire 14 is disposed within and extends through a second region 274 of the first plane 218. A first geometric form 207 of the third wire 205 is disposed within and extends through a third region 276 of the first plane 218. The first geometric forms 12A, 14A, 207 of the first, second, and third wires 12, 14, 205 collectively form the first plate 16.

Within the first plane 218, the first region 272 is adjacent to the second region 274, with a common border 277 formed by the first and second wires 12, 14. The first region 272 is also adjacent to the third region 276, with a common border 278 formed by the first and third wires 12, 205. In addition, the third region 276 is also adjacent to the second region 274, with a common border 279 formed by the second and third wires 14, 205.

Similarly, the second geometric form 12B of the first wire 12, the second geometric form 14B of the second wire 14, and a second geometric form of the third wire 205 would likewise be disposed within and extend through three similar adjacent, non-overlapping regions of the second plane 220, collectively forming the second plate 18 (not depicted in FIG. 22). The various first and second components of the first, second, and third wires 12, 14, and 205 are preferably curved with an arch, such as is shown in FIG. 22. Similar combinations of any number of different amounts of wires can similarly be used to form any number of different forms.

As mentioned above, in certain embodiments, the occluder device 10 may include multiple hubs 30, for example as depicted in FIG. 15. The number and configuration of such multiple hubs 30 may vary in different embodiments. In one such embodiment, a first end of the first wire 12 is disposed at a first hub 30, and at least one of the second end of the first wire 12, the first end of the second wire 14, and/or the second end of the second wire 14 is disposed at a second hub (such as hub 119 of FIGS. 12B, 13, and/or 15). In one such exemplary embodiment, the first and second ends of the first wire 12 are disposed at the first hub 30, and the first and second ends of the second wire 14 are disposed at the second hub (such as the second hub 119 of FIG. 15). In another such exemplary embodiment, the first ends of the first and second wires 12, 14 are disposed at the first hub 30, and the second ends of the first and second wires 12, 14 are disposed at the second hub (such as the hub 119 of FIGS. 12B, 13, and/or 15), among other possible variations.

Figure 23A:
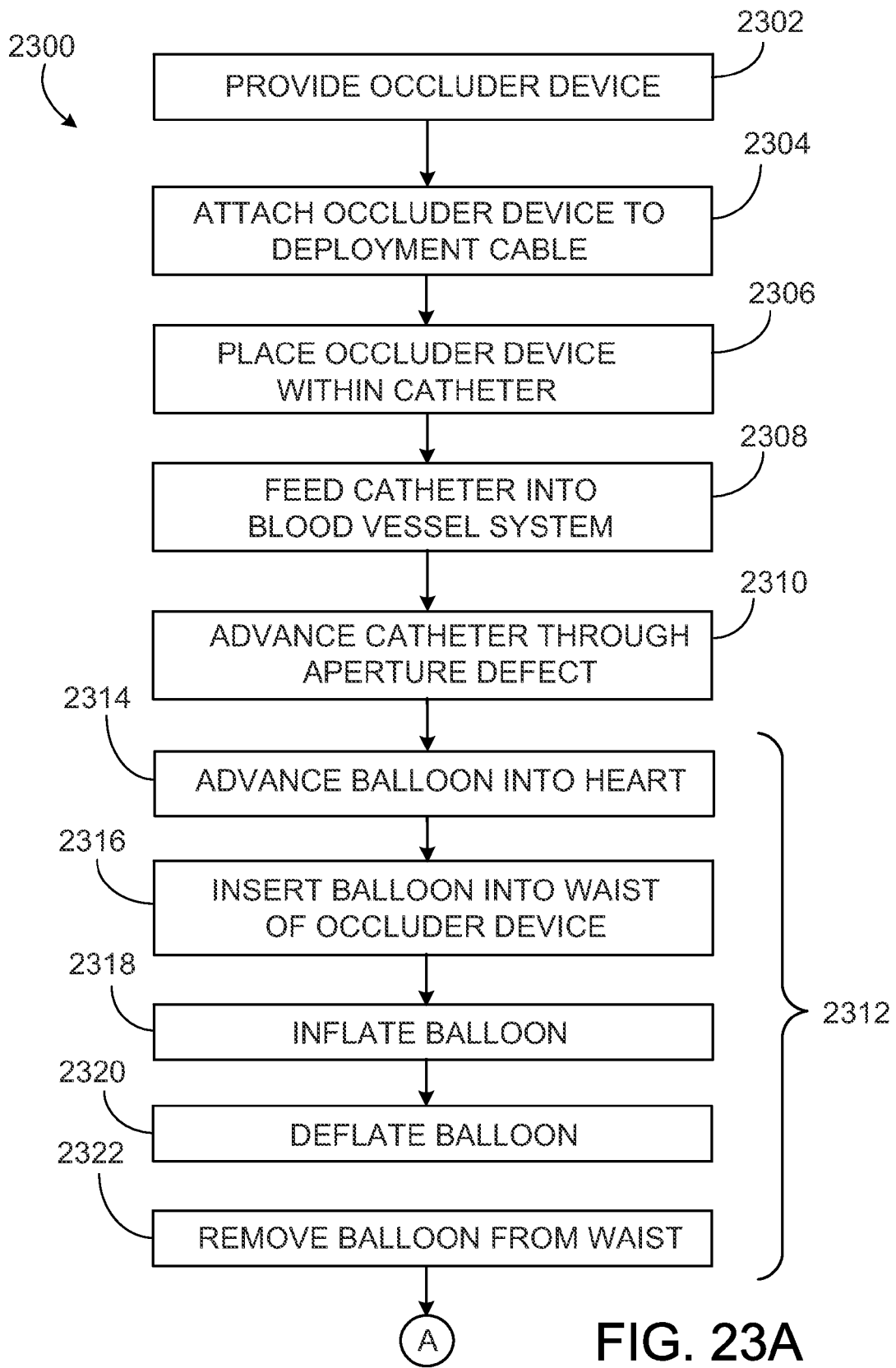
FIG. 23 is a flowchart of an exemplary embodiment of a method for occluding an aperture defect in a heart to prevent the flow of blood therethrough, and that may be implemented using the occluder devices of FIGS. 2-22.
Figure 23B:
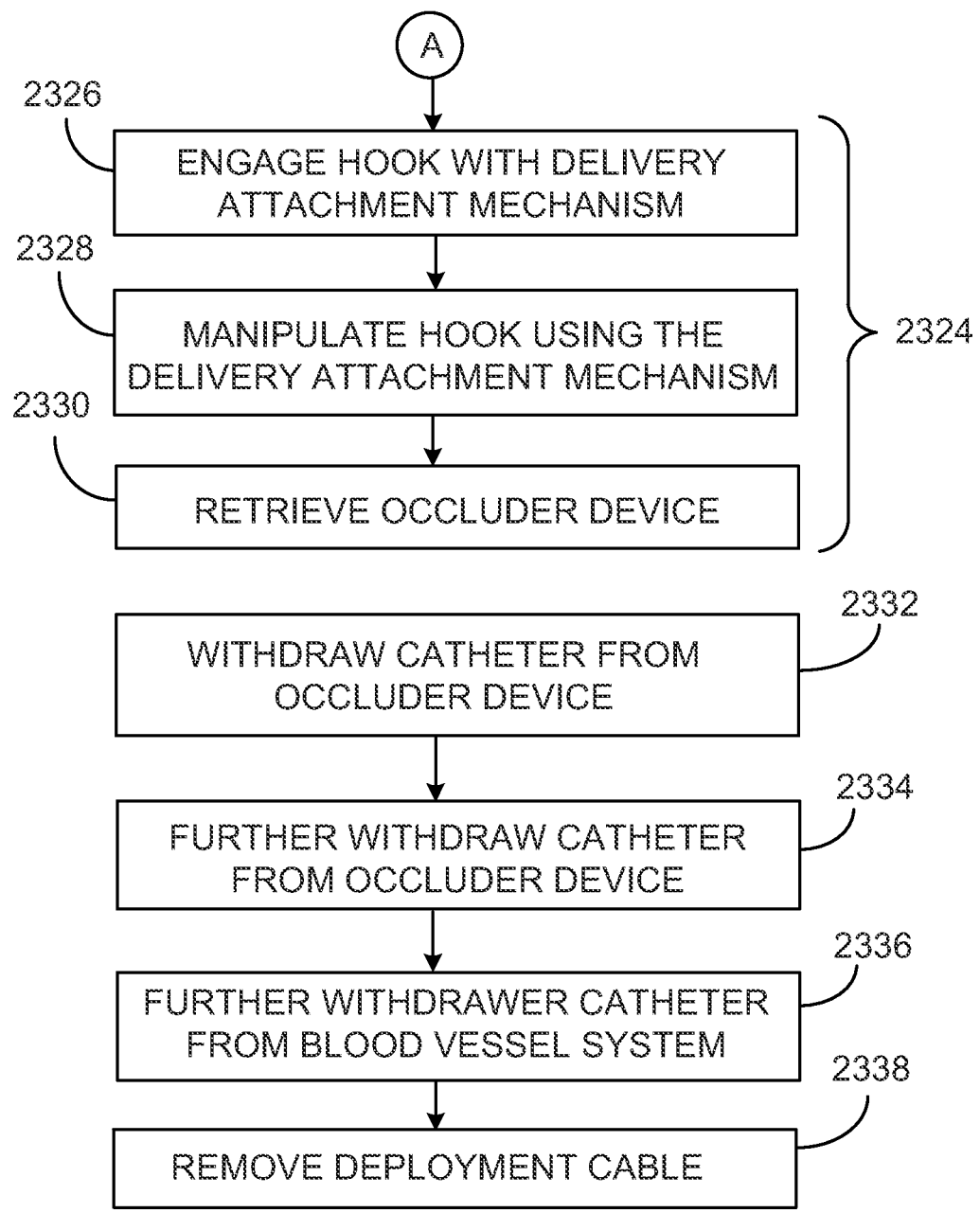

FIG. 23 is a flowchart of an exemplary embodiment of a method 2300 for occluding an aperture defect in a heart. The method 2300 can be utilized in connection with the heart 1 of FIG. 1 and the various embodiments of the occluder device 10 of FIGS. 2-22. Specifically, the method 2300 preferably utilizes one or more embodiments of the occluder devices 10 of FIGS. 2-22 to occlude an aperture defect of a heart, such as the aperture defect 6A of the heart 1 depicted in FIG. 1.

As depicted in FIG. 23, the method 2300 includes the step of providing an occluder device (step 2302). In various embodiments, the occluder device corresponds to the occluder device 10 depicted in any of the embodiments depicted in FIGS. 2-22 and/or described above. The occluder device preferably comprises a first flexible wire (such as wire 12 described above) and a second flexible wire (such as wire 14 described above). Each of the first and second wires is comprised of a shape memory material. Each of the first and second wires is shaped into first and second geometric forms (such as forms 12A, 12B, 14A, and 14B described above) around an inner region such that the first geometric form of the first wire and the first geometric form of the second wire form a first plate (such as plate 16 described above) in a first plane, and the second geometric form 12B of the first wire 12 and the second geometric form 14B of the second wire 14 form a second plate (such as plate 18 described above) in a second plane that is parallel to and remote from the first plane. The first and second plates are separated by a waist (such as waist 20 described above) formed from two portions of the first wire and two portions of the second wire. A sealed covering (such as covering 24A or 24B described above) is preferably disposed over at least one of the first and second plates. The covering provides a seal for the aperture defect (such as the defect 6A of the heart 1 described above). Each of the first and second wires has a first end and a second end. Each of the first and second ends of the first and second wires are connected to a hub (such as hub 30 described above). The hub further comprises a delivery attachment mechanism (for example, that includes or is used in connection with the catheter 40 described above) for attachment to a removable deployment cable (such as deployment cable 34 described above).

The method 2300 also includes the step of attaching the occluder device to the removable deployment cable (step 2304). The occluder device is placed within a flexible delivery catheter (such as the catheter 40 described above) having an open channel (such as the channel 42 described above) (step 2306). The catheter is fed into a blood vessel system (such as a blood vessel system of the heart 1 described above) and advanced via the blood vessel system to the aperture defect in the heart (step 2308). The catheter, with the occluder device disposed within, is similarly advanced through the aperture defect (step 2310).

In certain optional embodiments, a balloon sub-process 2312 is also utilized in occluding the aperture defect in the heart. In one such embodiment, depicted in FIG. 23, a balloon is advanced into the heart through the open channel toward the occluder device at the aperture defect (step 2314). The balloon is also inserted into the waist of the occluder device (step 2316). The balloon is then inflated (step 2318), in order to help position the occluder device proximate the heart defect. Once the occluder device is properly positioned, the balloon is deflated (step 2320) and then removed from the waist of the occluder device (step 2322).

In other optional embodiments, a hook sub-process 2324 may be utilized in occluding the aperture defect in the heart. In one such embodiment, depicted in FIG. 23, a hook (such as one or more of the hooks 136, 232 described above), is engaged with the delivery attachment mechanism (such as the catheter) (step 2326), preferably via a screw system. The hook is manipulated using the delivery attachment mechanism and used to reposition the occluder device (step 2328). In certain embodiments, the hook may also be utilized to retrieve the occluder device by exerting force on the delivery attachment mechanism in a direction away from the heart (step 2330).

The catheter next is withdrawn from the occluder device (step 2332). Preferably, the catheter is withdrawn from the occluder device in step 2332 in a manner such that the first plate of the occluder device expands on a first side of the aperture defect. In addition, the catheter is further withdrawn from the occluder device such that the second plate of the occluder device expands on a second side of the aperture defect (step 2334). Preferably, the catheter is withdrawn from the occluder device in step 2334 in a manner, such that the waist of the occluder device expands by memory retention within the aperture defect to self-center the occluder device. The catheter is then withdrawn from the blood vessel system (step 2336), and the deployment cable is removed from the hub of the occluder device (step 2338).

It will be appreciated that certain steps of the method 2300 may vary in certain embodiments. It will also be appreciated that certain steps of the method 2300 may occur in a different order than is depicted in FIG. 23. For example, the optional hook sub-process 2324 may be used before the optional balloon sub-process 2312. It will similarly be appreciated that certain steps of the method 230 may occur simultaneously with one another.

Other embodiments may comprise any combinations of the embodiments described herein and/or described in the drawings. It is understood that the disclosure is not confined to the particular construction and arrangement of parts herein illustrated and described, but embraces such modified forms thereof as come within the scope of the following claims. Additionally, it will be appreciated that various embodiments may be freely combined together, and/or that various features of different embodiments may be freely combined together.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

We claim:

1. A device for occluding an aperture in tissue, the device comprising:
   a first flexible wire;
   a second flexible wire, wherein each of the first and second wires is comprised of a shape memory material, wherein each of the first and second wires has a first and a second end; and
   a hub, wherein each of the first and second ends of the first and second wires are connected to the hub,
   wherein each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is remote from the first plane, and
   wherein the first and second plates are separated by a waist, the waist comprising a first waist portion and a second waist portion, the first waist portion having a first length, and the second waist portion having a second length that is greater than the first length.

2. The device of claim 1, wherein the first geometric forms of the first and second wires are generally semi-circular.

3. The device of claim 1, wherein:
   the first plate comprises a first disc; and
   the second plate comprises a second disc.

4. The device of claim 1, further comprising:
   a covering over the first plate, the second plate, or both that provides a seal to occlude the aperture.

5. The device of claim 1, wherein the waist is self-centering.

6. The device of claim 1, wherein:
   the first waist portion has a first waist surface area; and
   the second waist portion has a second waist surface area that is greater than the first waist surface area.

7. A device for occluding an aperture in tissue, the device comprising:
   a first flexible wire;
   a second flexible wire, wherein each of the first and second wires is comprised of a shape memory material, wherein each of the first and second wires has a first and a second end; and
   a hub, wherein each of the first and second ends of the first and second wires are connected to the hub,
   wherein each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is remote from the first plane, and wherein the first and second plates are separated by a waist comprising:
   a first segment of the first wire, the first segment of the first wire having a first length;
   a second segment of the first second wire, a length of the second segment of the first wire being substantially equal to the first length;
   a first segment of the second wire, the first segment of the second wire having a second length that is greater than the first length; and
   a second segment of the second wire, a length of the second segment of the second wire being substantially equal to the second length.

8. The device of claim 7, wherein at least one of the first segment of the first wire, the second segment of the first wire, the first segment of the second wire, and the second segment of the second wire comprises an arc segment.

9. The device of claim 7, wherein each of the first segment of the first wire, the second segment of the first wire, the first segment of the second wire, and the second segment of the second wire comprises an arc segment.

10. The device of claim 7, wherein the first geometric forms of the first and second wires are generally semi-circular.

11. The device of claim 7, wherein:
    the first plate comprises a first disc; and
    the second plate comprises a second disc.

12. The device of claim 7, further comprising:
    a covering over the first plate, the second plate, or both that provides a seal to occlude the aperture.

13. The device of claim 7, wherein the waist is self-centering.

14. A device for occluding an aperture in tissue, the device comprising:
    a first flexible wire;
    a second flexible wire, wherein each of the first and second wires is comprised of a shape memory material, wherein each of the first and second wires has a first and a second end; and
    a hub, wherein each of the first and second ends of the first and second wires are connected to the hub,
    wherein each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is remote from the first plane, and
    wherein the first and second plates are separated by a waist formed from two portions of the first wire and two portions of the second wire, the first plate and the second plate forming a non-zero angle with respect to one another.

15. The device of claim 14, wherein the non-zero angle is greater than five degrees.

16. The device of claim 14, wherein the non-zero angle is greater than ten degrees.

17. The device of claim 14, wherein the non-zero angle is approximately equal to twenty degrees.

18. The device of claim 14, wherein the first geometric forms of the first and second wires are generally semi-circular.

19. The device of claim 14, wherein:
    the first plate comprises a first disc; and
    the second plate comprises a second disc.

20. The device of claim 14, further comprising:
    a covering over the first plate, the second plate, or both that provides a seal to occlude the aperture.

21. The device of claim 14, wherein the waist is self-centering.

22. A device for occluding an aperture in tissue, the device comprising:
    a first flexible wire;
    a second flexible wire, wherein each of the first and second wires is comprised of a shape memory material, wherein each of the first and second wires has a first and a second end; and a hub, wherein each of the first and second ends of the first and second wires are connected to the hub, wherein each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is remote from the first plane, and wherein the first and second plates are not substantially parallel to one another and are separated by a waist formed from two portions of the first wire and two portions of the second wire.

23. The device of claim 22, wherein the first geometric forms of the first and second wires are generally semi-circular.

24. The device of claim 22, wherein:
the first plate comprises a first disc; and
the second plate comprises a second disc.

25. The device of claim 22, further comprising:
a covering over the first plate, the second plate, or both that provides a seal to occlude the aperture.

26. The device of claim 22, wherein the waist is self-centering.

27. A device for occluding an aperture in tissue, the device comprising:
a first flexible wire; and
a second flexible wire, wherein each of the first and second wires is comprised of a shape memory material, wherein each of the first and second wires has a first and a second end; and
a hub, wherein each of the first and second ends of the first and second wires are connected to the hub,
wherein each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is remote from the first plane, and
wherein the first and second plates are separated by a waist formed from a first waist component of the first wire and a second waist component of the second wire, the first and second waist components being of unequal sizes.

28. The device of claim 27, wherein:
the first waist component has a first length;
the second waist component has a second length; and
the second length is larger than the first length.

29. The device of claim 27, wherein:
the first waist component has a first surface area;
the second waist component has a second surface area; and
the second surface area is larger than the first surface area.

30. The device of claim 27, wherein:
the first waist component has a first radius;
the second waist component has a second radius; and
the second radius is larger than the first radius.

31. The device of claim 27, wherein the first geometric forms of the first and second wires are generally semi-circular.

32. The device of claim 27, wherein:
the first plate comprises a first disc; and
the second plate comprises a second disc.

33. The device of claim 27, further comprising:
a covering over the first plate, the second plate, or both that provides a seal to occlude the aperture.

34. The device of claim 27, wherein the waist is self-centering.

35. A device for occluding an aperture in tissue, the device comprising:
a first flexible wire; and
a second flexible wire, wherein each of the first and second wires is comprised of a shape memory material, wherein each of the first and second wires has a first and a second end; and
a hub, wherein each of the first and second ends of the first and second wires are connected to the hub,
wherein each of the first and second wires is shaped into first and second geometric forms such that the first geometric form of the first wire and the first geometric form of the second wire form a first plate in a first plane, and the second geometric form of the first wire and the second geometric form of the second wire form a second plate in a second plane that is remote from the first plane, and
wherein the first and second plates are separated by a waist formed from a first waist component of the first wire and a second waist component of the second wire, the first and second waist components configured to generate a non-zero angle of curvature for the waist.

36. The device of claim 35, wherein the angle of curvature is not equal to zero.

37. The device of claim 35, wherein the angle of curvature is greater than five degrees.

38. The device of claim 35, wherein the angle of curvature is greater than ten degrees.

39. The device of claim 35, wherein the angle of curvature is approximately equal to twenty degrees.

40. The device of claim 35, wherein the first geometric forms of the first and second wires are generally semi-circular.

41. The device of claim 35, wherein:
the first plate comprises a first disc; and
the second plate comprises a second disc.

42. The device of claim 35, further comprising:
a covering over the first plate, the second plate, or both that provides a seal to occlude the aperture.

43. The device of claim 35, wherein the waist is self-centering.

* * * * *